US012649747B2

(12) United States Patent
Qian et al.

(10) Patent No.: US 12,649,747 B2
(45) Date of Patent: Jun. 9, 2026

(54) SALT FORM AND CRYSTAL FORM OF PYRAZOLE SUBSTITUTED IMIDAZO[1,2-a]QUINOXALINE DERIVATIVE

(71) Applicant: OCUMENSION THERAPEUTICS (SUZHOU) CO., LTD, Suzhou City (CN)

(72) Inventors: Wenyuan Qian, Shanghai (CN); Hongjian Wang, Shanghai (CN); Liang Tan, Shanghai (CN); Shuhui Chen, Shanghai (CN)

(73) Assignee: OCUMENSION THERAPEUTICS (SUZHOU) CO., LTD, Suzhou City (CN)

( * ) Notice: Subject to any disclaimer, the term of this patent is extended or adjusted under 35 U.S.C. 154(b) by 495 days.

(21) Appl. No.: 18/264,061

(22) PCT Filed: Jan. 12, 2022

(86) PCT No.: PCT/CN2022/071598

§ 371 (c)(1),
(2) Date: Aug. 2, 2023

(87) PCT Pub. No.: WO2022/166548

PCT Pub. Date: Aug. 11, 2022

(65) Prior Publication Data

US 2024/0132503 A1 Apr. 25, 2024

(30) Foreign Application Priority Data

Feb. 3, 2021 (CN) ......................... 202110151592.7

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
None
See application file for complete search history.

(56) References Cited

U.S. PATENT DOCUMENTS

2023/0219960 A1* 7/2023 Qian ....................... A61P 13/12 540/575

FOREIGN PATENT DOCUMENTS

| | | | | |
|---|---|---|---|---|
| CN | 1609105 | A | 4/2005 | |
| CN | 102413831 | A | 4/2012 | |
| CN | 110194772 | A | 9/2019 | |
| CN | 109689641 | B | 11/2020 | |
| CN | 111819177 | B | 3/2022 | |
| WO | WO 99/09845 | A1 | 3/1999 | |
| WO | 2010135571 | A1 | 11/2010 | |
| WO | WO 2012/143143 | A1 | 10/2012 | |
| WO | 2021169958 | A1 | 9/2021 | |
| WO | WO 2021/169958 | * | 9/2021 | ........... C07D 487/04 |

OTHER PUBLICATIONS

CAS RN 68009-09-6 (entered into STN on Nov. 16, 1984) (Year: 1984).*
Extended European Search Report mailed Feb. 12, 2025 in European Application No. 22748827.7, 9 pages.
International Search Report w/English translation for PCT/CN2022/071598 mailed Apr. 13, 2022, 6 pages.
Written Opinion of the ISA for PCT/CN2022/071598 mailed Apr. 13, 2022, 6 pages.
Chinese Office Action mailed Dec. 31, 2024 in Chinese Application No. 202280008264.4, with English translation, 8 pages.
Chinese Office Action mailed Apr. 21, 2025 in Chinese Application No. 202280008264.4, with English translation, 7 pages.

* cited by examiner

*Primary Examiner* — Craig D Ricci
(74) *Attorney, Agent, or Firm* — Nixon & Vanderhye P.C.

(57) ABSTRACT

Provided are a salt form and a crystal form of a pyrazole substituted imidazo[1,2-a]quinoxaline derivative, and a preparation method therefor. Specifically disclosed are a salt form and a crystal form of a compound of formula (I), and a preparation method therefor and the use thereof in the preparation of drugs related to dual inhibitors of spleen tyrosine kinase (Syk) and vascular endothelial growth factor 2 (VEGFR2).

(I)

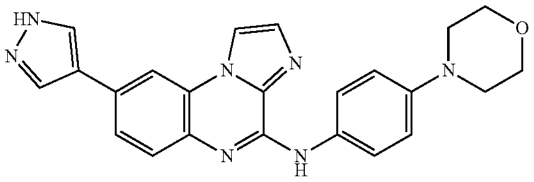

17 Claims, 11 Drawing Sheets

SALT FORM AND CRYSTAL FORM OF PYRAZOLE SUBSTITUTED IMIDAZO[1,2-a]QUINOXALINE DERIVATIVE

CROSS-REFERENCE TO RELATED APPLICATIONS

The present application claims priority to Patent Application No. CN202110151592.7, filed on Feb. 3, 2021, and entitled "SALT FORM AND CRYSTAL FORM OF PYRAZOLE-SUBSTITUTED IMIDAZO[1,2-A]QUINOXALINE DERIVATIVE", which is incorporated herein by reference in its entirety.

TECHNICAL FIELD

The present disclosure relates to a salt form and a crystal form of a pyrazole-substituted imidazo[1,2-a]quinoxaline derivative and a preparation method of the same.

BACKGROUND

Spleen tyrosine kinase (Syk) is an intracellular tyrosine protein kinase belonging to a ZAP70 protein kinase family, and is crucial in early development of B cells, ontogeny of lymphocytes, and the functioning of mature B cells. In these processes, Syk participates in various signal transduction pathways and can function without being phosphorylated via Src kinase. Syk is expressed in non-hematopoietic cells such as epithelial cells, liver cells, fibroblasts, nerve cells and breast tissue in addition to hematopoietic stem cells, and has multiple functions. Dysfunctions of Syk PTK exist in many human diseases such as allergic reactions, asthma, inflammations and autoimmune diseases, and many studies have revealed that Syk is an important mediator in acute or chronic inflammations.

VEGFR2, also known as KDR or Flk-1, is identified as a receptor of VEGF and VEGFC, which serves as an early marker of endothelial cell progenitor cells, and is exclusively expressed in endothelial cells in vivo. VEGFR2 has been shown to be a main signal transducer for angiogenesis and development of pathological conditions (for example, cancer and diabetic retinopathy). Studies have shown that anti-VEGF can inhibit expression and activation of pro-inflammatory factors, thereby reducing ocular surface inflammation. VEGFR2 transduces the main signal of angiogenesis by virtue of its strong tyrosine kinase activity. However, unlike other representative tyrosine kinase receptors, VEGFR2 does not use a Ras pathway for main downstream signaling. Instead, VEGFR2 uses the phospholipase C-protein kinase C pathway for mitogen-activated protein (MAP) kinase activation and DNA synthesis. Therefore, inhibiting VEGFR2 activity and its downstream signaling is a crucial target for the treatment of diseases involving angiogenesis, inflammations, and so on.

Therefore, Syk and VEGFR-2 activity can be inhibited for treating allergic diseases, autoimmune diseases and inflammatory diseases, including, but not limited to, dry eye disease and allergic conjunctivitis, retinal inflammatory disease, age-related macular degeneration (AMD), proliferative diabetic retinopathy (PDR), retinopathy of prematurity (ROP), cancer, rheumatoid arthritis, glomerulonephritis, multiple vasculitides, idiopathic thrombocytopenia purpura (ITP), myasthenia gravis, allergic rhinitis, chronic obstructive pulmonary disease (COPD), adult respiratory distress syndrome (ARDs) and asthma.

SUMMARY

The present disclosure provides a crystal form A of a compound of formula (I), where an X-ray powder diffraction pattern of the crystal form A under Cu Kα radiation has characteristic diffraction peaks at 2θ angles of 11.96±0.20°, 14.14±0.20°, 16.76±0.20°, 17.55±0.20°, and 21.84±0.20°, (I)

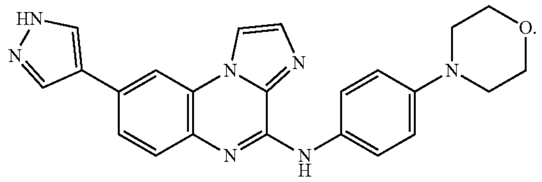

In some embodiments of the present disclosure, an X-ray powder diffraction pattern of the crystal form A under Cu Kα radiation has characteristic diffraction peaks at 2θ angles of 11.96±0.20°, 14.14±0.20°, 15.36±0.20°, 16.76±0.20°, 17.55±0.20°, 21.84±0.20°, 23.49±0.20°, and 24.42±0.20°.

In some embodiments of the present disclosure, an X-ray powder diffraction pattern of the crystal form A under Cu Kα radiation has characteristic diffraction peaks at 2θ angles of 11.96±0.20°, 14.14±0.20°, 15.36±0.20°, 16.76±0.20°, 17.55±0.20°, 21.25±0.20°, 21.84±0.20°, 23.49±0.20°, 24.42±0.20°, 28.37±0.20°, and 30.15±0.20°.

In some embodiments of the present disclosure, an X-ray powder diffraction pattern of the crystal form A under Cu Kα radiation has characteristic diffraction peaks at 2θ angles of 11.96±0.20°, 14.14±0.20°, and 16.76±0.20°, and may also have characteristic diffraction peaks at 15.36±0.20°, and/or 17.55±0.20°, and/or 21.25±0.20°, and/or 21.84±0.20°, and/or 23.49±0.20°, and/or 24.42±0.20°, and/or 28.37±0.20°, and/or 30.15±0.20°.

In some embodiments of the present disclosure, an X-ray powder diffraction pattern of the crystal form A under Cu Kα radiation has characteristic diffraction peaks at 2θ angles of 11.96°, 14.14°, 15.36°, 16.21°, 16.76°, 17.55°, 17.96°, 21.25°, 21.84°, 23.49°, 24.42°, 28.37°, and 30.15°.

In some embodiments of the present disclosure, an XRPD pattern of the crystal form A is shown in FIG. 1.

In some embodiments of the present disclosure, in the XRPD pattern of the crystal form A under Cu Kα radiation, the peak positions and relative intensities of the diffraction peaks are shown in Table 1 below:

TABLE 1

XRPD Diffraction Data of the Crystal Form A of the Compound of Formula (I)

| No. | Diffraction angle 2θ | Relative intensity (%) |
|---|---|---|
| 1 | 9.60 | 1.50 |
| 2 | 11.96 | 100.00 |
| 3 | 14.14 | 18.69 |
| 4 | 15.36 | 4.01 |
| 5 | 16.21 | 3.44 |
| 6 | 16.76 | 26.46 |
| 7 | 17.55 | 11.61 |
| 8 | 17.96 | 6.62 |
| 9 | 18.47 | 1.81 |
| 10 | 21.25 | 5.50 |
| 11 | 21.84 | 7.63 |
| 12 | 22.32 | 2.00 |

TABLE 1-continued

| XRPD Diffraction Data of the Crystal Form A of the Compound of Formula (I) | | |
|---|---|---|
| No. | Diffraction angle 2θ | Relative intensity (%) |
| 13 | 23.49 | 5.06 |
| 14 | 24.42 | 5.07 |
| 15 | 25.20 | 1.54 |
| 16 | 26.34 | 0.86 |
| 17 | 27.36 | 0.59 |
| 18 | 28.37 | 4.50 |
| 19 | 29.17 | 2.47 |
| 20 | 30.15 | 4.09 |

In some embodiments of the present disclosure, a differential scanning calorimetry (DSC) curve of the crystal form A has an endothermic peak at 332.4° C.±3° C.

In some embodiments of the present disclosure, a differential scanning calorimetry (DSC) curve of the crystal form A has endothermic peaks at 283.7° C.±3° C. and 332.4° C.±3° C.

In some embodiments of the present disclosure, a DSC pattern of the crystal form A is shown in FIG. 2.

In some embodiments of the present disclosure, a thermal gravimetric analysis (TGA) curve of the crystal form A has a weight loss of 2.41±0.20% at 250.0° C.±3° C.

In some embodiments of the present disclosure, a TGA pattern of the crystal form A is shown in FIG. 3.

The present disclosure further provides a crystal form B of a compound of formula (I), where an X-ray powder diffraction pattern of the crystal form B under Cu Kα radiation has characteristic diffraction peaks at 2θ angles of 12.14±0.20°, 19.52±0.20°, 22.08±0.20°, and 28.22±0.20°, (I)

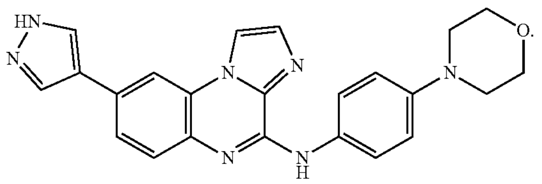

In some embodiments of the present disclosure, an X-ray powder diffraction pattern of the crystal form B under Cu Kα radiation has characteristic diffraction peaks at 2θ angles of 11.35±0.20°, 12.14±0.20°, 14.69±0.20°, 18.26±0.20°, 19.52±0.20°, 22.08±0.20°, and 28.21±0.20°.

In some embodiments of the present disclosure, an X-ray powder diffraction pattern of the crystal form B under Cu Kα radiation has characteristic diffraction peaks at 2θ angles of 11.35±0.20°, 12.14±0.20°, 14.69±0.20°, 16.70±0.20°, 18.26±0.20°, 19.52±0.20°, 22.08±0.20°, 26.55±0.20°, 27.31±0.20°, and 28.21±0.20°.

In some embodiments of the present disclosure, an XRPD pattern of the crystal form B is shown in FIG. 4.

In some embodiments of the present disclosure, in the XRPD pattern of the crystal form B under Cu Kα radiation, the peak positions and relative intensities of the diffraction peaks are shown in Table 2 below:

TABLE 2

| XRPD Diffraction Data of the Crystal Form B of the Compound of Formula (I) | | |
|---|---|---|
| No. | Diffraction angle 2θ | Relative intensity (%) |
| 1 | 11.35 | 18.38 |
| 2 | 12.14 | 74.61 |
| 3 | 14.69 | 17.61 |
| 4 | 16.70 | 19.27 |
| 5 | 18.26 | 23.72 |
| 6 | 19.52 | 23.69 |
| 7 | 22.08 | 100.00 |
| 8 | 24.46 | 1.94 |
| 9 | 26.55 | 5.98 |
| 10 | 27.31 | 3.28 |
| 11 | 28.22 | 23.88 |
| / | / | / |

In some embodiments of the present disclosure, a differential scanning calorimetry (DSC) curve of the crystal form B has an endothermic peak at 331.8±3° C.

In some embodiments of the present disclosure, a DSC pattern of the crystal form B is shown in FIG. 5.

In some embodiments of the present disclosure, a thermal gravimetric analysis (TGA) curve of the crystal form B has a weight loss of 4.11±0.20% at 300.0° C.±3° C.

In some embodiments of the present disclosure, a TGA pattern of the crystal form B is shown in FIG. 6.

The present disclosure further provides a preparation method of a crystal form B, where the method comprises the following steps:

(a) dissolving the crystal form A of the compound of formula (I) in dimethylacetamide;

(b) placing an opened glass vial containing the solution of the compound in a glass bottle filled with acetone in advance;

(c) sealing the glass bottle and allowing gas and liquid permeation at 20° C. to 30° C. for three days;

(d) removing a supernatant with a straw, and drying a remaining solid at room temperature in the bottle which is opened for five days to obtain the solid;

(e) adding the solid into an aluminum crucible with a cover and slowly heating the solid to 150° C. under an atmosphere of dry nitrogen; and (f) cooling the solid down to 20° C. to 30° C.

The present disclosure further provides a pharmaceutically acceptable salt of a compound of formula (I), where the pharmaceutically acceptable salt is a hydrate, maleate or gentisate, (I)

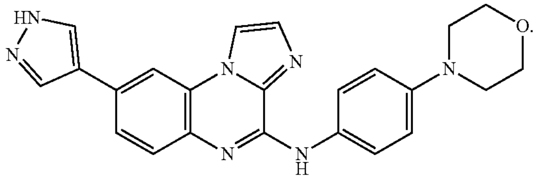

In some embodiments of the present disclosure, the pharmaceutically acceptable salt of the compound of formula (I) is a hydrate, maleate or gentisate, and has a structure represented by formula (II), formula (III) or formula (IV),

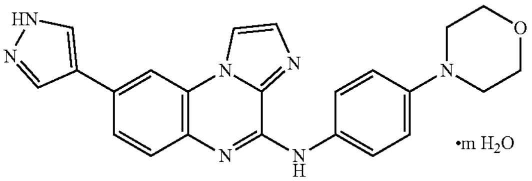
(II)
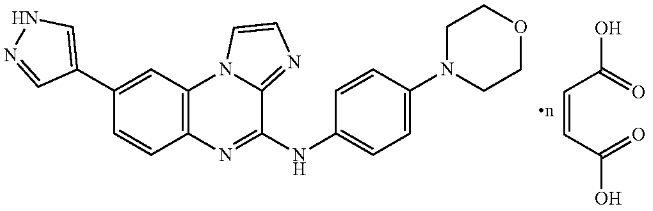
(III)
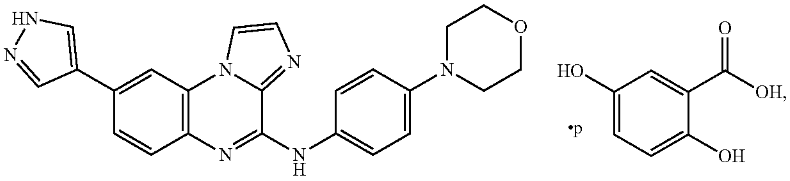
(IV)
wherein, m is selected from 3.0 to 5.0, n is selected from 0.7 to 1.3, and p is selected from 0.7 to 1.3.
In some embodiments of the present disclosure, m is selected from 3.0, 3.5, 4.0, 4.1, 4.2, 4.3, 4.4, 4.5, 4.6, 4.7, 4.8, 4.9, and 5.0; n is selected from 0.7, 0.8, 0.9, 1.0, 1.1, 1.2, and 1.3; and p is selected from 0.7, 0.8, 0.9, 1.0, 1.1, 1.2, and 1.3.
In some embodiments of the present disclosure, the compound of formula (II), formula (III) or formula (IV) is selected from the group consisting of:
(II-1)
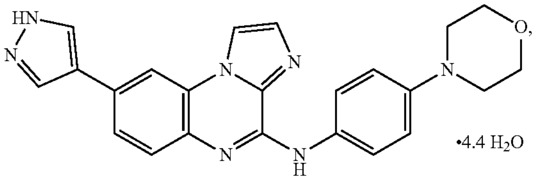
(III-1)
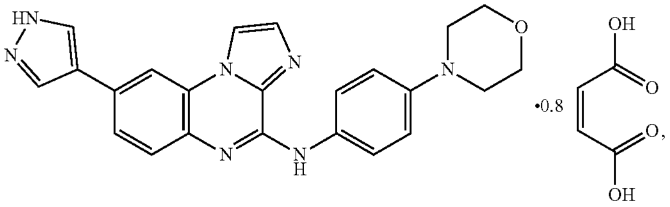
and
(IV-1)
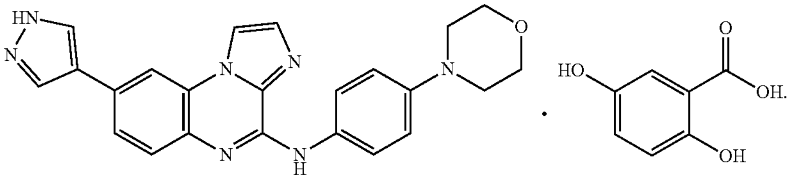

The present disclosure further provides a crystal form C of a compound of formula (II-1), where an X-ray powder diffraction pattern of the crystal form C under Cu Kα radiation has characteristic diffraction peaks at 2θ angles of 6.53±0.20°, 12.05±0.20°, and 13.05±0.20°.

(II-1)

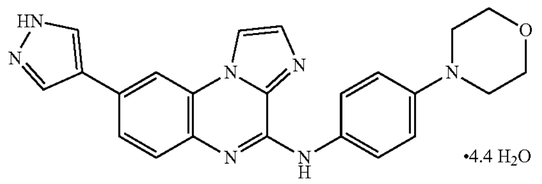

In some embodiments of the present disclosure, an X-ray powder diffraction pattern of the crystal form C under Cu Kα radiation has characteristic diffraction peaks at 2θ angles of 6.53±0.20°, 12.05±0.20°, 13.05±0.20°, 20.87±0.20°, and 24.02±0.20°.

In some embodiments of the present disclosure, an X-ray powder diffraction pattern of the crystal form C under Cu Kα radiation has characteristic diffraction peaks at 2θ angles of 6.53°, 12.05°, 13.05°, 14.84°, 17.89°, 20.87°, 24.02°, and 26.84°.

In some embodiments of the present disclosure, the X-ray powder diffraction pattern of the crystal form C is shown in FIG. 7.

In some embodiments of the present disclosure, in the XRPD pattern of the crystal form C under Cu Kα radiation, peak positions and relative intensities of the diffraction peaks are shown in Table 3 below:

TABLE 3

XRPD Diffraction Data of the Crystal Form C of the Compound of Formula (II-1)

| No. | Diffraction angle 2θ | Relative intensity (%) |
|---|---|---|
| 1 | 6.53 | 100.00 |
| 2 | 12.05 | 5.83 |
| 3 | 13.05 | 33.09 |
| 4 | 14.39 | 0.62 |
| 5 | 14.84 | 1.66 |
| 6 | 15.48 | 0.44 |
| 7 | 16.34 | 0.73 |
| 8 | 17.14 | 0.51 |
| 9 | 17.89 | 1.45 |
| 10 | 19.14 | 0.39 |
| 11 | 20.87 | 3.31 |
| 12 | 21.22 | 0.88 |
| 13 | 21.95 | 0.58 |
| 14 | 23.15 | 0.75 |
| 15 | 24.02 | 3.12 |
| 16 | 24.87 | 0.50 |
| 17 | 26.84 | 1.34 |
| 18 | 28.44 | 0.62 |
| 19 | 29.78 | 0.27 |
| 20 | 32.93 | 0.20 |

In some embodiments of the present disclosure, a differential scanning calorimetry (DSC) curve of the crystal form C has endothermic peaks at 58.8±3° C. and 331.4±3° C.

In some embodiments of the present disclosure, a DSC pattern of the crystal form C is shown in FIG. 8.

The present disclosure further provides a preparation method of the crystal form C, where the method includes the following steps:

(a) dissolving the crystal form A of the compound of formula (I) in tetrahydrofuran and water (4:1 by volume);

(b) performing filtration with a polytetrafluoroethylene filter membrane; and (c) allowing slow evaporation of a filtrate from the filtration at 20° C. to 30° C. for 3 days to obtain a solid when a solvent is removed by the evaporation.

The present disclosure further provides a crystal form D of a compound of formula (III-1), where an X-ray powder diffraction pattern of the crystal form D under Cu Kα radiation has characteristic diffraction peaks at 2θ angles of 7.26±0.20°, 11.99±0.20°, 12.72±0.20°, and 14.52±0.20°, (III-1)

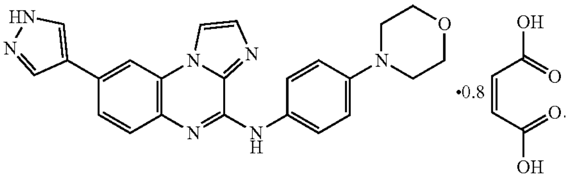

In some embodiments of the present disclosure, an X-ray powder diffraction pattern of the crystal form D under Cu Kα radiation has characteristic diffraction peaks at 2θ angles of 7.26±0.20°, 10.06±0.20°, 11.99±0.20°, 12.72±0.20°, 14.52±0.20°, 16.17±0.20°, and 20.23±0.20°.

In some embodiments of the present disclosure, an X-ray powder diffraction pattern of the crystal form D under Cu Kα radiation has characteristic diffraction peaks at 2θ angles of 7.26±0.20°, 10.06±0.20°, 11.99±0.20°, 12.72±0.20°, 14.52±0.20°, 16.17±0.20°, 16.75±0.20°, 20.23±0.20°, 20.83±0.20°, and 24.09±0.20°.

In some embodiments of the present disclosure, the X-ray powder diffraction pattern of the crystal form D is shown in FIG. 9.

In some embodiments of the present disclosure, in the XRPD pattern of the crystal form D under Cu Kα radiation, peak positions and relative intensities of the diffraction peaks are shown in Table 4 below:

TABLE 4

XRPD Diffraction Data of the Crystal Form D of the Compound of Formula (III-1)

| No. | Diffraction angle 2θ | Relative intensity (%) |
|---|---|---|
| 1 | 7.26 | 92.65 |
| 2 | 10.06 | 16.92 |
| 3 | 11.99 | 88.18 |
| 4 | 12.72 | 100.00 |
| 5 | 14.52 | 58.74 |
| 6 | 16.17 | 25.28 |
| 7 | 16.75 | 16.75 |
| 8 | 20.23 | 32.56 |
| 9 | 20.83 | 11.64 |
| 10 | 24.09 | 15.46 |

In some embodiments of the present disclosure, a differential scanning calorimetry (DSC) curve of the crystal form D has endothermic peaks at 72.0° C.±3° C., 136.0° C.±3° C. and 207.0° C.±3° C.

In some embodiments of the present disclosure, a DSC pattern of the crystal form D is shown in FIG. 10.

In some embodiments of the present disclosure, a thermal gravimetric analysis (TGA) curve of the crystal form D has a weight loss of 4.73±0.20% at 150.0° C.±3° C.

In some embodiments of the present disclosure, a TGA pattern of the crystal form D is shown in FIG. 11.

In some embodiments of the present disclosure, an $^1H$ NMR pattern of the crystal form D is shown in FIG. 12.

The present disclosure further provides a crystal form E of a compound of formula (IV-1), where an X-ray powder diffraction pattern of the crystal form E under Cu Kα radiation has characteristic diffraction peaks at 2θ angles of 12.20±0.20°, 18.73±0.20°, 22.20±0.20°, 24.10±0.20°, and 24.58±0.20°, In some embodiments of the present disclosure, a differential scanning calorimetry (DSC) curve of the crystal form E has endothermic peaks at 97.2±3° C. and 291.4±3° C.

In some embodiments of the present disclosure, a DSC pattern of the crystal form E is shown in FIG. 14.

In some embodiments of the present disclosure, a thermal gravimetric analysis (TGA) curve of the crystal form E has a weight loss of 6.72±0.20% at 150.0° C.±3° C.

In some embodiments of the present disclosure, a TGA pattern of the crystal form E is shown in FIG. 15.

In some embodiments of the present disclosure, an $^1H$ NMR pattern of the crystal form E is shown in FIG. 16.

(IV-1)

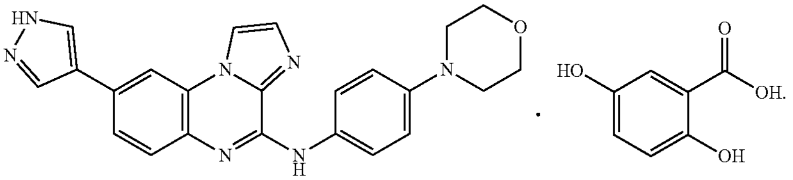

In some embodiments of the present disclosure, an X-ray powder diffraction pattern of the crystal form E under Cu Kα radiation has characteristic diffraction peaks at 2θ angles of 7.47±0.20°, 12.20±0.20°, 13.72±0.20°, 18.73±0.20°, 22.20±0.20°, 24.10±0.20°, 24.58±0.20°, and 27.62±0.20°.

In some embodiments of the present disclosure, an X-ray powder diffraction pattern of the crystal form E under Cu Kα radiation has characteristic diffraction peaks at 2θ angles of 7.47±0.20°, 10.61±0.20°, 12.20±0.20°, 13.72±0.20°, 14.99±0.20°, 18.73±0.20°, 19.53±0.20°, 20.83±0.20°, 22.20±0.20°, 24.10±0.20°, 24.58±0.20°, and 27.62±0.20°.

In some embodiments of the present disclosure, the X-ray powder diffraction pattern of the crystal form E is shown in FIG. 13.

In some embodiments of the present disclosure, in the XRPD pattern of the crystal form E under Cu Kα radiation, the peak positions and relative intensities of the diffraction peaks are shown in Table 5 below:

TABLE 5

XRPD Diffraction Data of the Crystal Form E of the Compound of Formula (IV-1)

| No. | Diffraction angle 2θ | Relative intensity (%) |
|---|---|---|
| 1 | 7.47 | 51.52 |
| 2 | 10.61 | 18.87 |
| 3 | 12.20 | 58.82 |
| 4 | 13.72 | 28.41 |
| 5 | 14.99 | 24.52 |
| 6 | 18.73 | 81.31 |
| 7 | 19.53 | 22.15 |
| 8 | 20.83 | 24.53 |
| 9 | 22.20 | 100.00 |
| 10 | 23.02 | 19.49 |
| 11 | 24.10 | 66.49 |
| 12 | 24.58 | 48.32 |
| 13 | 27.62 | 32.52 |
| 14 | 28.35 | 18.41 |

In some embodiments of the present disclosure, a differential scanning calorimetry (DSC) curve of the crystal form E has an endothermic peak at 291.4±3° C.

The present disclosure further provides a pharmaceutically acceptable salt of the compound of formula (I), where the pharmaceutically acceptable salt is hydrochloride, sulfate, phosphate, p-toluenesulfonate, or hydrobromide, (I)

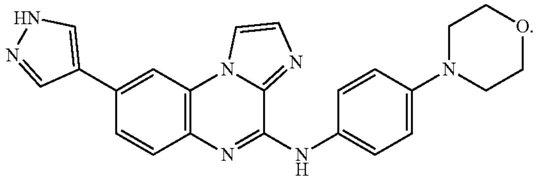

In some embodiments of the present disclosure, the pharmaceutically acceptable salt of the compound of formula (I) is hydrochloride, sulfate, phosphate, p-toluenesulfonate, or hydrobromide, and has a structure represented by formula (V), formula (VI), formula (VII), formula (VIII) or formula (IX), (V)

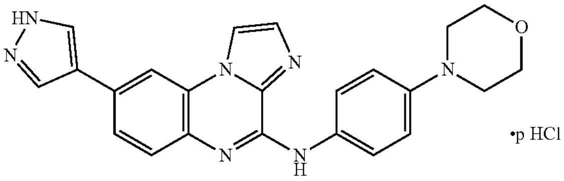

(VI)

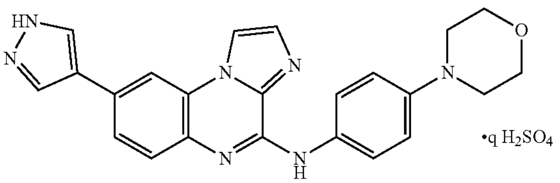

-continued (VII)

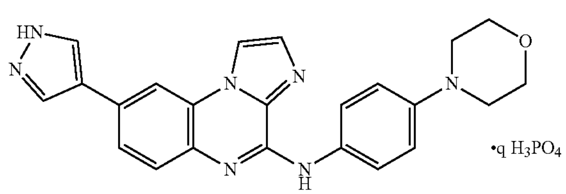

(VIII)

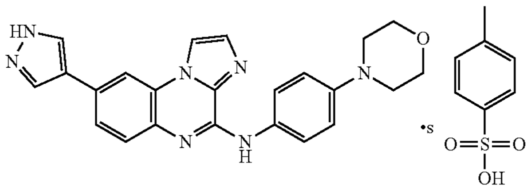

and (IX)

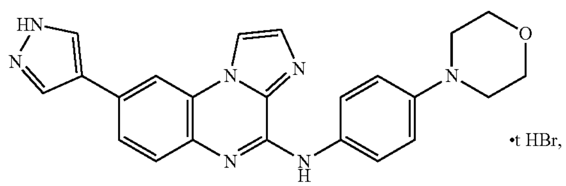

wherein, p is selected from 0.7 to 2.3, q is selected from 0.7 to 1.3, r is selected from 0.7 to 2.3, s is selected from 0.7 to 1.3, and t is selected from 0.7 to 2.3.

In some embodiments of the present disclosure, p is selected from 0.7, 0.8, 0.9, 1.0, 1.1, 1.2, 1.3, 1.4, 1.5, 1.6, 1.7, 1.8, 1.9, 2.0, 2.1, 2.2, and 2.3; q is selected from 0.7, 0.8, 0.9, 1.0, 1.1, 1.2, and 1.3; r selected from 0.7, 0.8, 0.9, 1.0, 1.1, 1.2, 1.3, 1.4, 1.5, 1.6, 1.7, 1.8, 1.9, 2.0, 2.1, 2.2, and 2.3; s selected from 0.7, 0.8, 0.9, 1.0, 1.1, 1.2, and 1.3; and t selected from 0.7, 0.8, 0.9, 1.0, 1.1, 1.2, 1.3, 1.4, 1.5, 1.6, 1.7, 1.8, 1.9, 2.0, 2.1, 2.2, and 2.3.

In some embodiments of the present disclosure, the compound of formula (V), formula (VI), formula (VII), formula (VIII) or formula (IX) has a structure represented by formula (V-1), formula (V-2), formula (VI-1), formula (VII-1), formula (VII-2), formula (VIII-1), formula (IX-1) or formula (IX-2), (V-1)

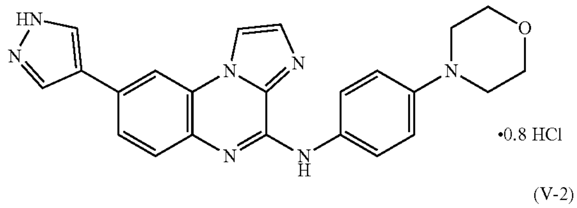

(V-2)

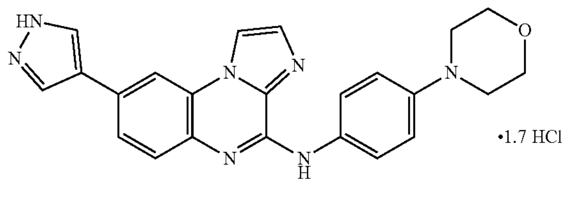

-continued (VI-1)

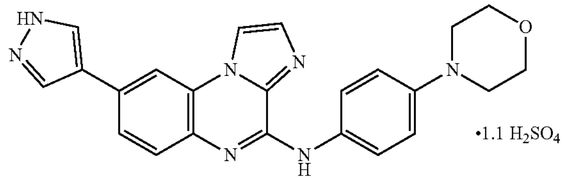

(VII-1)

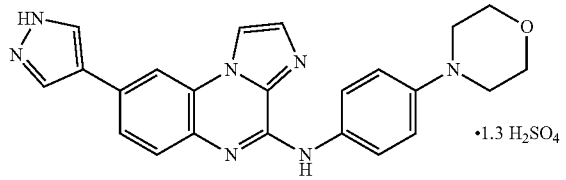

(VII-2)

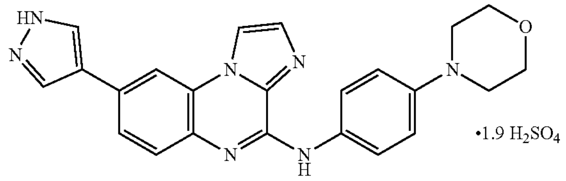

(VIII-1)

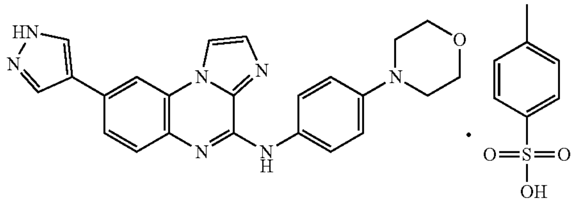

(IX-1)

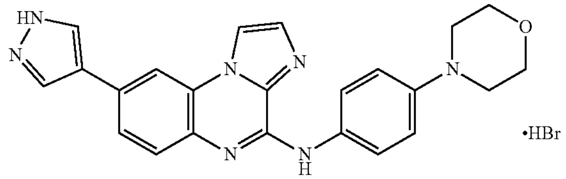

(IX-2)

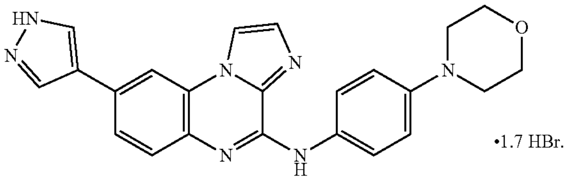

The present disclosure further provides a crystal form F of a compound of formula (V-1), where an X-ray powder diffraction pattern of the crystal form F under Cu Kα radiation has characteristic diffraction peaks at 2θ angles of 11.94±0.20°, 15.42±0.20°, and 16.71±0.20°.

In some embodiments of the present disclosure, an X-ray powder diffraction pattern of the crystal form F under Cu Kα radiation has characteristic diffraction peaks at 2θ angles of 9.42°, 11.94°, 14.11°, 15.42°, and 16.71°.

In some embodiments of the present disclosure, the X-ray powder diffraction pattern of the crystal form F is shown in FIG. 17.

In some embodiments of the present disclosure, in the XRPD pattern of the crystal form F under Cu Kα radiation, the peak positions and relative intensities of the diffraction peaks are shown in Table 6 below:

TABLE 6

XRPD Diffraction Data of the Crystal Form F of the Compound of Formula (V-1)

| No. | Diffraction angle 2θ | Relative intensity (%) |
|---|---|---|
| 1 | 9.42 | 8.28 |
| 2 | 11.94 | 100.00 |
| 3 | 14.11 | 18.06 |
| 4 | 15.42 | 27.54 |
| 5 | 16.71 | 20.52 |
| / | / | / |

The present disclosure further provides a crystal form G of a compound of formula (V-2), where an X-ray powder diffraction pattern of the crystal form G under Cu Kα radiation has characteristic diffraction peaks at 2θ angles of 7.08±0.20°, 7.94±0.20°, 12.59±0.20°, 20.35±0.20°, and 26.35±0.20°.

In some embodiments of the present disclosure, an X-ray powder diffraction pattern of the crystal form G under Cu Kα radiation has characteristic diffraction peaks at 2θ angles of 7.08±0.20°, 7.94±0.20°, 12.59±0.20°, 13.55±0.20°, 15.59±0.20°, 16.90±0.20°, 20.35±0.20°, and 26.35±0.20°.

In some embodiments of the present disclosure, an X-ray powder diffraction pattern of the crystal form G under Cu Kα radiation has characteristic diffraction peaks at 2θ angles of 6.77°, 7.08°, 7.94°, 11.80°, 12.59°, 13.55°, 15.59°, 16.90°, 17.74°, 20.35°, 22.66°, and 26.35°.

In some embodiments of the present disclosure, the X-ray powder diffraction pattern of the crystal form G is shown in FIG. 18.

In some embodiments of the present disclosure, in the XRPD pattern of the crystal form G under Cu Kα radiation, the peak positions and relative intensities of the diffraction peaks are shown in Table 7 below:

TABLE 7

XRPD Diffraction Data of the Crystal Form G of the Compound of Formula (V-2)

| No. | Diffraction angle 2θ | Relative intensity (%) |
|---|---|---|
| 1 | 6.77 | 86.90 |
| 2 | 7.08 | 93.23 |
| 3 | 7.94 | 86.93 |
| 4 | 11.80 | 26.48 |
| 5 | 12.59 | 100.00 |
| 6 | 13.55 | 43.40 |
| 7 | 15.59 | 50.56 |
| 8 | 16.90 | 42.68 |
| 9 | 17.74 | 21.97 |
| 10 | 20.35 | 84.11 |
| 11 | 22.66 | 29.21 |
| 12 | 26.35 | 61.38 |

The present disclosure further provides a crystal form H of a compound of formula (VI-1), where an X-ray powder diffraction pattern of the crystal form H under Cu Kα radiation has characteristic diffraction peaks at 2θ angles of 11.96±0.20°, 12.83±0.20°, 20.25±0.20°, and 20.95±0.20°.

In some embodiments of the present disclosure, an X-ray powder diffraction pattern of the crystal form H under Cu Kα radiation has characteristic diffraction peaks at 2θ angles of 11.96±0.20°, 12.83±0.20°, 13.45±0.20°, 16.75±0.20°, 20.25±0.20°, 20.95±0.20°, 24.02±0.20°, and 24.45±0.20°.

In some embodiments of the present disclosure, an X-ray powder diffraction pattern of the crystal form H under Cu Kα radiation has characteristic diffraction peaks at 2θ angles of 11.96°, 12.83°, 13.45°, 16.75°, 18.04°, 20.25°, 20.95°, 23.39°, 24.02°, and 24.45°.

In some embodiments of the present disclosure, the X-ray powder diffraction pattern of the crystal form H is shown in FIG. 19.

In some embodiments of the present disclosure, in the XRPD pattern of the crystal form H under Cu Kα radiation, the peak positions and relative intensities of the diffraction peaks are shown in Table 8 below:

TABLE 8

XRPD Diffraction Data of the Crystal Form H of the Compound of Formula (VI-1)

| No. | Diffraction angle 2θ | Relative intensity (%) |
|---|---|---|
| 1 | 11.96 | 81.80 |
| 2 | 12.83 | 100.00 |
| 3 | 13.45 | 30.83 |
| 4 | 16.75 | 35.78 |
| 5 | 18.04 | 33.00 |
| 6 | 20.25 | 48.57 |
| 7 | 20.95 | 47.43 |
| 8 | 23.39 | 14.30 |
| 9 | 24.02 | 26.75 |
| 10 | 24.45 | 32.89 |

The present disclosure further provides a crystal form I of a compound of formula (VII-1), where an X-ray powder diffraction pattern of the crystal form I under Cu Kα radiation has characteristic diffraction peaks at 2θ angles of 5.12±0.20°, 11.49±0.20°, 15.44±0.20°, 20.62±0.20°, and 21.98±0.20°.

In some embodiments of the present disclosure, an X-ray powder diffraction pattern of the crystal form I under Cu Kα radiation has characteristic diffraction peaks at 2θ angles of 5.12±0.20°, 11.49±0.20°, 15.44±0.20°, 18.58±0.20°, 20.62±0.20°, 21.98±0.20°, 22.98±0.20°, and 25.87±0.20°.

In some embodiments of the present disclosure, an X-ray powder diffraction pattern of the crystal form I under Cu Kα radiation has characteristic diffraction peaks at 2θ angles of 5.12±0.20°, 11.49±0.20°, 15.44±0.20°, 16.26±0.20°, 18.58±0.20°, 19.05±0.20°, 20.62±0.20°, 21.98±0.20°, 22.98±0.20°, 24.33±0.20°, 25.87±0.20°, and 27.23±0.20°.

In some embodiments of the present disclosure, the X-ray powder diffraction pattern of the crystal form I is shown in FIG. 20.

In some embodiments of the present disclosure, in the XRPD pattern of the crystal form I under Cu Kα radiation, the peak positions and relative intensities of the diffraction peaks are shown in Table 9 below:

TABLE 9

XRPD Diffraction Data of the Crystal Form I of the Compound of Formula (VII-1)

| No. | Diffraction angle 2θ | Relative intensity (%) |
|---|---|---|
| 1 | 5.12 | 81.30 |
| 2 | 11.49 | 100.00 |
| 3 | 15.44 | 37.76 |
| 4 | 16.26 | 7.29 |

TABLE 9-continued

| XRPD Diffraction Data of the Crystal Form I of the Compound of Formula (VII-1) | | |
|---|---|---|
| No. | Diffraction angle 2θ | Relative intensity (%) |
| 5 | 18.58 | 18.17 |
| 6 | 19.05 | 12.59 |
| 7 | 20.62 | 70.68 |
| 8 | 21.98 | 30.71 |
| 9 | 22.98 | 11.86 |
| 10 | 24.33 | 13.73 |
| 11 | 25.87 | 30.19 |
| 12 | 27.23 | 11.30 |
| 13 | 31.12 | 8.12 |
| / | / | / |

The present disclosure further provides a crystal form J of a compound of formula (VII-2), where an X-ray powder diffraction pattern of the crystal form J under Cu Kα radiation has characteristic diffraction peaks at 2θ angles of 13.24±0.20°, 24.70±0.20°, and 25.57±0.20°.

In some embodiments of the present disclosure, an X-ray powder diffraction pattern of the crystal form J under Cu Kα radiation has characteristic diffraction peaks at 2θ angles of 9.66±0.20°, 13.24±0.20°, 20.17±0.20°, 24.70±0.20°, and 25.57±0.20°.

In some embodiments of the present disclosure, an X-ray powder diffraction pattern of the crystal form J under Cu Kα radiation has characteristic diffraction peaks at 2θ angles of 9.66±0.20°, 13.24±0.20°, 14.53±0.20°, 16.06±0.20°, 18.90±0.20°, 20.17±0.20°, 24.70±0.20°, and 25.57±0.20°.

In some embodiments of the present disclosure, the X-ray powder diffraction pattern of the crystal form J is shown in FIG. 21.

In some embodiments of the present disclosure, in the XRPD pattern of the crystal form J under Cu Kα radiation, peak positions and relative intensities of the diffraction peaks are shown in Table 10 below:

TABLE 10

| XRPD Diffraction Data of the Crystal Form J of the Compound of Formula (VII-2) | | |
|---|---|---|
| No. | Diffraction angle 2θ | Relative intensity (%) |
| 1 | 9.66 | 48.22 |
| 2 | 13.24 | 56.97 |
| 3 | 14.53 | 39.90 |
| 4 | 16.06 | 44.89 |
| 5 | 18.90 | 41.86 |
| 6 | 20.17 | 48.38 |
| 7 | 24.70 | 100.00 |
| 8 | 25.57 | 75.44 |

The present disclosure further provides a crystal form K of a compound of formula (VIII-1), where an X-ray powder diffraction pattern of the crystal form K under Cu Kα radiation has characteristic diffraction peaks at 2θ angles of 4.89±0.20°, 9.78±0.20°, and 16.04±0.20°.

In some embodiments of the present disclosure, an X-ray powder diffraction pattern of the crystal form K under Cu Kα radiation has characteristic diffraction peaks at 2θ angles of 4.89°, 9.78°, 10.42°, 12.05°, 14.71°, and 16.04°.

In some embodiments of the present disclosure, the X-ray powder diffraction pattern of the crystal form K is shown in FIG. 22.

In some embodiments of the present disclosure, in the XRPD pattern of the crystal form K under Cu Kα radiation, the peak positions and relative intensities of the diffraction peaks are shown in Table 11 below:

TABLE 11

| XRPD Diffraction Data of the Crystal Form K of the Compound of Formula (VIII-1) | | |
|---|---|---|
| No. | Diffraction angle 2θ | Relative intensity (%) |
| 1 | 4.89 | 100.00 |
| 2 | 9.78 | 15.52 |
| 3 | 10.42 | 7.38 |
| 4 | 12.05 | 6.77 |
| 5 | 14.71 | 12.15 |
| 6 | 16.04 | 14.57 |

The present disclosure further provides a crystal form L of a compound of formula (VIII-1), where an X-ray powder diffraction pattern of the crystal form L under Cu Kα radiation has characteristic diffraction peaks at 2θ angles of 4.62±0.20°, 13.87±0.20°, and 18.52±0.20°.

In some embodiments of the present disclosure, an X-ray powder diffraction pattern of the crystal form L under Cu Kα radiation has characteristic diffraction peaks at 2θ angles of 4.62±0.20°, 13.87±0.20°, 18.52±0.20°, 19.17±0.20°, and 23.23±0.20°.

In some embodiments of the present disclosure, an X-ray powder diffraction pattern of the crystal form L under Cu Kα radiation has characteristic diffraction peaks at 2θ angles of 4.62°, 13.87°, 18.52°, 19.17°, 19.73°, 21.21°, 23.23°, 25.41°, 32.26°, and 34.34°.

In some embodiments of the present disclosure, the X-ray powder diffraction pattern of the crystal form L is shown in FIG. 23.

In some embodiments of the present disclosure, in the XRPD pattern of the crystal form L under Cu Kα radiation, the peak positions and relative intensities of the diffraction peaks are shown in Table 12 below:

TABLE 12

| XRPD Diffraction Data of the Crystal Form L of the Compound of Formula (VIII-1) | | |
|---|---|---|
| No. | Diffraction angle 2θ | Relative intensity (%) |
| 1 | 4.62 | 100.00 |
| 2 | 13.87 | 16.24 |
| 3 | 18.52 | 23.87 |
| 4 | 19.17 | 11.36 |
| 5 | 19.73 | 5.09 |
| 6 | 21.21 | 4.90 |
| 7 | 23.23 | 7.11 |
| 8 | 25.41 | 5.35 |
| 9 | 32.26 | 2.03 |
| 10 | 34.34 | 3.03 |

The present disclosure further provides a crystal form M of a compound of formula (IX-1), where an X-ray powder diffraction pattern of the crystal form M under Cu Kα radiation has characteristic diffraction peaks at 2θ angles of 10.01±0.20°, 11.95±0.20°, and 23.57±0.20°.

In some embodiments of the present disclosure, an X-ray powder diffraction pattern of the crystal form M under Cu Kα radiation has characteristic diffraction peaks at 2θ angles of 10.01±0.20°, 11.95±0.20°, 14.12±0.20°, 16.72±0.20°, and 23.57±0.20°.

In some embodiments of the present disclosure, an X-ray powder diffraction pattern of the crystal form M under Cu Kα radiation has characteristic diffraction peaks at 2θ angles of 10.01°, 11.95°, 14.12°, 16.72°, 17.57°, 21.63°, and 23.57°.

In some embodiments of the present disclosure, the X-ray powder diffraction pattern of the crystal form M is shown in FIG. 24.

In some embodiments of the present disclosure, in the XRPD pattern of the crystal form M under Cu Kα radiation, the peak positions and relative intensities of the diffraction peaks are shown in Table 13 below:

TABLE 13

XRPD Diffraction Data of the Crystal Form M of the Compound of Formula (IX-1)

| No. | Diffraction angle 2θ | Relative intensity (%) |
|---|---|---|
| 1 | 10.01 | 81.98 |
| 2 | 11.95 | 100.00 |
| 3 | 14.12 | 26.73 |
| 4 | 16.72 | 39.24 |
| 5 | 17.57 | 33.42 |
| 6 | 21.63 | 38.31 |
| 7 | 23.57 | 39.58 |
| / | / | / |

The present disclosure further provides a crystal form N of a compound of formula (IX-2), where an X-ray powder diffraction pattern of the crystal form N under Cu Kα radiation has characteristic diffraction peaks at 2θ angles of 11.95±0.20°, 17.68±0.20°, 23.87±0.20°, 26.47±0.20°, and 27.04±0.20°.

In some embodiments of the present disclosure, an X-ray powder diffraction pattern of the crystal form N under Cu Kα radiation has characteristic diffraction peaks at 2θ angles of 11.95±0.20°, 15.42±0.20°, 17.68±0.20°, 18.16±0.20°, 23.87±0.20°, 25.60±0.20°, 26.47±0.20°, and 27.04±0.20°.

In some embodiments of the present disclosure, an X-ray powder diffraction pattern of the crystal form N under Cu Kα radiation has characteristic diffraction peaks at 2θ angles of 6.62±0.20°, 11.95±0.20°, 15.42±0.20°, 17.68±0.20°, 18.16±0.20°, 19.26±0.20°, 23.87±0.20°, 25.60±0.20°, 26.47±0.20°, 27.04±0.20°, and 28.33±0.20°.

In some embodiments of the present disclosure, the X-ray powder diffraction pattern of the crystal form N is shown in FIG. 25.

In some embodiments of the present disclosure, in the XRPD pattern of the crystal form N under Cu Kα radiation, the peak positions and relative intensities of the diffraction peaks are shown in Table 14 below:

TABLE 14

XRPD Diffraction Data of the Crystal Form N of the Compound of Formula (IX-2)

| No. | Diffraction angle 2θ | Relative intensity (%) |
|---|---|---|
| 1 | 6.62 | 26.46 |
| 2 | 11.95 | 67.45 |
| 3 | 15.42 | 46.12 |
| 4 | 17.68 | 60.08 |
| 5 | 18.16 | 35.97 |
| 6 | 19.26 | 20.31 |
| 7 | 23.87 | 50.14 |
| 8 | 25.60 | 27.42 |
| 9 | 26.47 | 100.00 |
| 10 | 27.04 | 62.82 |
| 11 | 28.33 | 23.28 |
| / | / | / |

The present disclosure further provides use of the crystal form A, the crystal form B, the crystal form C, the crystal form D or the crystal form E in preparation of a spleen tyrosine kinase (Syk) and vascular endothelial growth factor 2 (VEGFR2) dual inhibitor-related drug.

Technical Effect

The crystal forms of the compounds of the present disclosure have good inhibitory activity on both Syk and KDR (VEGFR-2) and have good pharmacokinetic properties, including a good eye-to-blood ratio, tissue exposure, etc. The preparation processes of the salt forms and the crystal forms of the compounds of the present disclosure are simple, and the crystal forms are stable and less affected by heat and light, and are easy to prepare.

Definitions and Explanation

Unless otherwise stated, terms and phrases used below in the description have the following meanings. A specific phrase or term that is not specifically defined should not be considered to be indeterminate or unclear, but should be understood as a common meaning. A commodity name herein is intended to refer to a corresponding commodity or an active ingredient thereof.

An intermediate compound in the present disclosure can be prepared in various synthesis methods well known to persons skilled in the art, including specific embodiments listed below, embodiments formed in combination with other chemical synthesis methods, and equivalent replacements and so on known to persons skilled in the art. Preferred embodiments include but are not limited to examples of the present disclosure.

Chemical reactions in the specific embodiments of the present disclosure are completed in a suitable solvent, and the solvent should be a reagent and a material that are suitable for chemical changes in the present disclosure and meet requirements thereof. In order to obtain the compound in the present disclosure, persons skilled in the art need to modify or select synthesis steps or reaction procedures based on existing embodiments.

The present disclosure is specifically described via examples below, and these examples do not indicate any limitation on the present disclosure.

A structure of the compound in the present disclosure can be confirmed in conventional methods known to persons skilled in the art. If the present disclosure involves an absolute configuration of the compound, the absolute configuration can be confirmed in a conventional technical means in the art. For example, during single crystal X-ray diffraction (SXRD), the diffraction intensity data of a cultured single crystal is collected with a Bruker D8 venture diffractometer, a light source is Cu Kα radiation, and a scanning method is φ/ω scanning. After relevant data is collected, a crystal structure is further analyzed in a direct method (Shelxs97), which can ensure the absolute configuration.

The following abbreviations are used in the present disclosure:

ACN stands for acetonitrile; and DMSO stands for dimethylsulfoxide. $N_2$: nitrogen; RH: relative humidity; mL: milliliter; L: liter; min: minute; ° C.: degree Celsius; μm: micrometer; mm: millimeter; μL: microliter; moL/L: mole per liter; mg: milligram; s: second; nm: nanometer; MPa: megapascal; lux: lux; μw/$cm^2$: microwatt per square centimeter; h: hour; Kg: kilogram; nM: nanomole, rpm: revolutions per minute; XRPD stands for X-ray powder diffraction; DSC stands for differential scanning calorimetry; TGA stands for thermal gravimetric analysis; and $^1$H NMR stands for proton nuclear magnetic resonance.

The compound in the present disclosure is named based on a conventional naming principle in the art or by using ChemDraw® software, and a name in the supplier catalogue is used for a commercially available compound. All solvents used in the present disclosure are commercially available.

Instrument and Analysis Method of the Present Disclosure

1.1. X-Ray Powder Diffraction (XRPD) Method

Test method: About 10 mg of sample is used for XRPD detection.

Detailed XRPD instrument information and parameters are shown in Table 15 below:

TABLE 15

XRPD Instrument Information and Parameters

| Compound | Instrument Information |
|---|---|
| Crystal form A; and crystal forms C to N; | Instrument model: PANalytical X'Pert$^3$ X-ray powder diffractometer<br>Light pipe: Cu, Kα1 (Å): 1.540598; Kα2 (Å): 1.544426;<br>Kα2/Kα1 intensity ratio: 0.50;<br>Light pipe voltage: 45 kV;<br>Light pipe current: 40 mA;<br>Divergence slit: 1/8 degree<br>Scanning mode: continuous;<br>Scanning range: 3 to 40 deg;<br>Step: 0.0263 deg<br>Scanning time per step: 46.665 seconds |
| Crystal form B | Instrument model: PANalytical Empyrean X-ray powder diffractometer<br>Light pipe: Cu, Kα1 (Å): 1.540598; Kα2 (Å): 1.544426<br>Kα2/Kα1 intensity ratio: 0.50<br>Light pipe voltage: 45 kV<br>Light pipe current: 40 mA<br>Divergence slit: automatic<br>Scanning mode: continuous<br>Scanning range: 3 to 40 deg<br>Step: 0.0167 deg<br>Scanning time per step: 17.780 seconds |

1.2. Differential Scanning Calorimetry (DSC) Method

Detailed DSC instrument information and test method are shown in Table 16 below:

TABLE 16

DSC Instrument Information and Test Method

| Compound | Instrument information and test method |
|---|---|
| Crystal form A, crystal form B, and crystal form C | Instrument model: Discovery DSC 2500 differential scanning calorimeter<br>Test method: A sample (1 to 5 mg) was taken and added into a DSC aluminum crucible for testing. Under conditions of 50 mL/min and $N_2$, the sample was heated from 25° C. to 350° C. at a heating rate of 10° C./min. |
| Crystal form D | Instrument model: Q200 differential scanning calorimeter<br>Test method: A sample (1 to 5 mg) was taken and added into a DSC aluminum crucible for testing. Under conditions of 50 mL/min and $N_2$, the sample was heated from room temperature to 300° C.-310° C. at a heating rate of 10° C./min. |
| Crystal form E | Instrument model: Discovery DSC 2500 differential scanning calorimeter<br>Test method: A sample (1 to 5 mg) was taken and added into a DSC aluminum crucible for testing. Under conditions of 50 mL/min and $N_2$, the sample was heated from 25° C. to 295° C.-340° C. at a heating rate of 10° C./min. |

1.3. Thermal Gravimetric Analysis (TGA)

Detailed TGA instrument information and test method are shown in Table 17 below:

TABLE 17

TGA Instrument Information and Test Method

| Compound | Instrument information and test method |
|---|---|
| Crystal form A | Instrument model: Q5000 thermal gravimetric analyzer<br>Test method: A sample (2 to 5 mg) was taken and added into a TGA aluminum crucible for testing. Under conditions of 25 mL/min and $N_2$, the sample was heated from room temperature to 350° C. at a heating rate of 10° C./min. |
| Crystal form B and crystal form C | Instrument model: Discovery TGA 5500 thermal gravimetric analyzer<br>Test method: A sample (2 to 5 mg) was taken and added into a TGA aluminum crucible for testing. Under conditions of 25 mL/min and $N_2$, the sample was heated from room temperature to 350° C. at a heating rate of 10° C./min. |
| Crystal form D and crystal form E | Instrument model: Discovery TGA 5500 thermal gravimetric analyzer<br>Test method: A sample (2 to 5 mg) was taken and added into a TGA aluminum crucible for testing. Under conditions of 25 mL/min and $N_2$, the sample was heated from room temperature to 350° C. at a heating rate of 10° C./min. The sample was heated from 25° C. to 295° C.-340° C. at a heating rate of 10° C./min. |

1.4. High Performance Liquid Chromatography (HPLC)

High performance liquid chromatograph (Agilent 1260 HPLC)

Column: Waters Xbridge C18, 150×4.6 mm, 5 microns 12.2. Chromatographic Conditions Mobile phase A: 0.1% trifluoroacetic acid in aqueous solution;

Mobile phase B: 0.1% trifluoroacetic acid in acetonitrile;

Column temperature: 40° C.;

Flow rate: 1 mL/min;

Test wavelength: 254 nm;

Injection volume: 10 μL;

Test time: 10 minutes;

Diluent: ACN/$H_2O$ (4:1, v v)

A gradient program is shown in Table 18 below:

TABLE 18

| HPLC Gradient | |
|---|---|
| Time (min) | Mobile phase B (%) |
| 0.0 | 5 |
| 6.0 | 80 |
| 8.0 | 80 |
| 8.1 | 5 |

DETAILED DESCRIPTION

Figure 1:
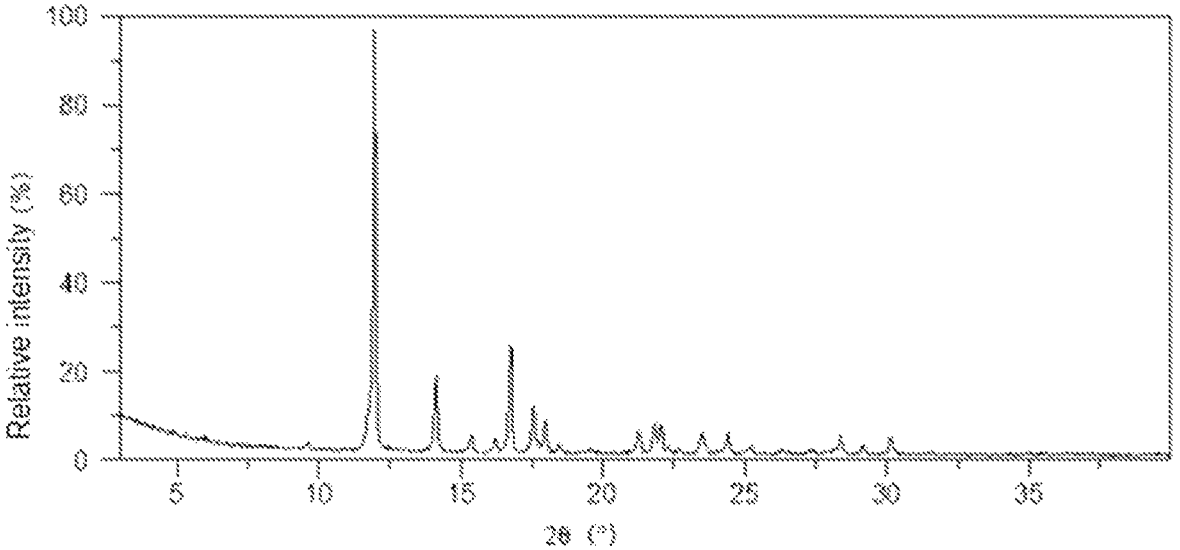
FIG. 1 is an XRPD pattern of a crystal form A of a compound of formula (I)

The following examples are used to describe the present disclosure in detail, but do not imply any unfavorable limitation on the present disclosure. The present disclosure is described in detail herein, and specific embodiments are also disclosed. Various changes and improvements made to the specific embodiments of the present disclosure without departing from the spirit and scope of the present disclosure are obvious to persons skilled in the art.

PREPARATION EXAMPLES

Example 1 Preparation of Crystal Form A of Compound of Formula (I)

(I)

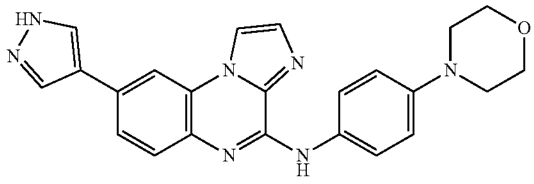

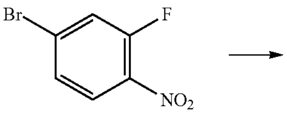

1a

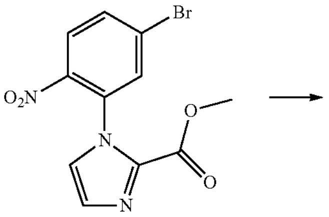

1b

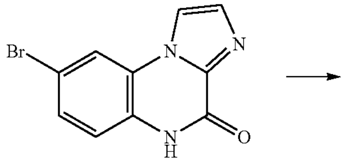

1c

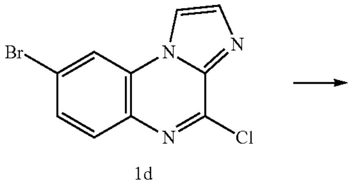

1d

-continued

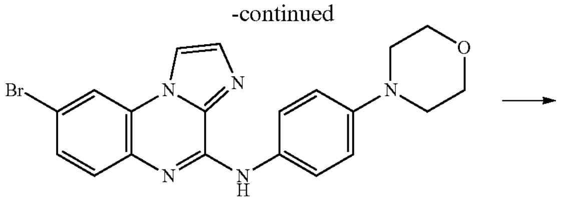

1e

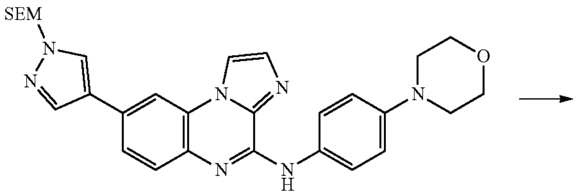

1f

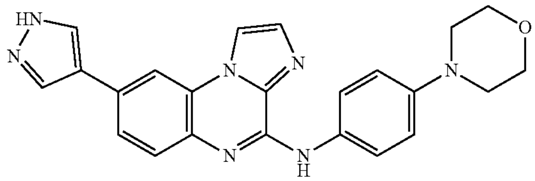

(1)

Step 1

16 L of dimethyl sulfoxide was first added to a reactor with a volume of 50 L. Mechanical stirring was started with a rotation speed of 150 rpm at an internal temperature shown as 15° C. Then 1950 g of compound 1a, 1230 g of 1H-imidazole-2-carboxylate methyl ester and 1880 g of sodium carbonate were added in sequence, heating was started, and an external heating temperature was set to 82° C. After stirring at an internal temperature of 78° C.-80° C. for 16 hours, the heating was ended, and the reaction solution was cooled to 30° C. The reaction solution was slowly added into 30 L of water while being stirred, and a large amount of yellow solid was precipitated. The external temperature was set to 10° C. and a resulting mixture was stirred for 50 minutes at 100 rpm. Filtration was started at an internal temperature shown as 15° C. to obtain a filtered solid which was vacuum-dried to obtain compound 1b.

$^1$NMR (400 MHz, DMSO-$d_6$) δ ppm 8.12 (d, J=8.5 Hz, 1H), 8.04 (d, J=J=2.0 Hz, 1H), 7.98-7.93 (m, 1H), 7.45 (s, 1H), 7.09 (s, 1H), 3.86 (s, 3H).

Step 2

18 L of ethanol and 4.5 L of water were first added to a reactor with a volume of 50 L. Stirring was started with a rotation speed of 150 rpm at an internal temperature shown as 15° C. Then 1665 g of the compound 1b, 1656 g of thiourea dioxide and 859.5 g of sodium bicarbonate were added in sequence. Heating was started, an external heating temperature was set to 65° C., and gas was discharged when the internal temperature rose to 60° C.-65° C. The temperature was maintained for 1 hour, and when no gas was discharged any more, the external temperature was raised to 80° C. After stirring for 16 hours, the heating was ended, and the reaction solution was cooled to 25° C. The reaction solution was slowly added into 25 L of water in two batches separately while being stirred, and a large amount of solid was precipitated. The external temperature was set to 10° C., after 30 minutes of stirring, filtration was started at an internal temperature shown as 15° C. The precipitated solid was added back into the reactor, stirring was started, 30 L of water was added, the internal temperature was raised to 65° C. via heating, and after 16 hours of stirring, the reaction solution was filtered immediately to obtain a filter cake which was vacuum-dried to obtain compound 1c.

$^1$H NMR (400 MHz, DMSO-$d_6$) δ ppm 11.95 (s, 1H), 8.61 (d, J=1.0 Hz, 1H), 8.45 (d, J=2.0 Hz, 1H), 7.62-7.54 (m, 1H), 7.34-7.25 (m, 1H).

Step 3

After an exhaust gas absorption device was established, 13.5 L of 1,4-dioxane was added to a reactor with a volume of 50 L. Stirring was started with a rotation speed of 150 rpm at an internal temperature shown as 15° C. Heating was started, an external heating temperature was set to 40° C., and then 900 g of the compound 1c and 825.98 g of N,N-dimethylaniline were added in sequence. 2610 g of phosphorus oxychloride was added dropwise with a constant pressure dropping funnel, and the internal temperature was controlled between 35° C. and 40° C. After the addition of the phosphorus oxychloride, the reaction solution was stirred at an internal temperature of 90° C.-92° C. for 16 hours, then the heating was ended, and the reaction solution was cooled to 25° C. The reaction solution was slowly added into 15 L of water in batches while being stirred. The external temperature was set to 30° C., the reaction solution was stirred for 1 hour, and 4 M sodium hydroxide aqueous solution was slowly added at an internal temperature of 15° C.-20° C. to adjust pH to 7. After being heated to an internal temperature of 30° C., the reaction solution was stirred for 30 minutes again and filtered to obtain a filter cake which was vacuum-dried to obtain compound 1d.

$^1$H NMR (400 MHz, DMSO-$d_6$) δ=, 9.01 (s, 1H), 8.80 (d, J=2.0 Hz, 1H), 7.95 (d, J=8.8 Hz, 1H), 7.91 (s, 1H), 7.84 (dd, J=2.0, 8.8 Hz, 1H).

Step 4

9 L of dimethyl sulfoxide was added to a reactor with a volume of 50 L at 20° C. Stirring was started at a rotation speed of 150 rpm. 620.24 g of 4-morpholine aniline, 1124.4 g of N, N-diisopropylethanamine and 820.00 g of the compound id were added sequentially. The reaction solution was stirred for 24 hours at an internal temperature of 95° C.-100° C. The heating was ended, and the reaction solution was cooled to 25° C. The reaction solution was slowly added into 30 L of water while being stirred. The external temperature was set to 10° C., the reaction solution was stirred for 0.5 hours and filtered to obtain a filter cake which was put into the reactor again, and 9 L of isopropanol was added into the reactor. The reaction solution was stirred for 1 hour at an internal temperature of 82° C. The reaction solution was filtered immediately to obtain a filter cake which was washed with 2 L of hot isopropanol, and vacuum-dried at 40° C.-50° C. for 12 hours to obtain compound 1e.

$^1$H NMR (400 MHz, DMSO-$d_6$) δ ppm 9.65 (s, 1H), 8.74 (d, J=1.0 Hz, 1H), 8.48 (s, 1H), 7.99 (d, J=9.0 Hz, 2H), 7.59-7.55 (m, 2H), 7.08-6.91 (m, 3H), 3.78-3.72 (m, 4H), 3.10-3.05 (m, 4H).

Step 5

4 L of dimethyltetrahydrofuran was added to a reactor with a volume of 50 L. Stirring was started at a rotation speed of 150 rpm. An external temperature was set to 5° C. 500.00 g of 4-pyrazoleboronic acid pinacol ester, 333.00 g of N,N-diisopropylethanamine were added sequentially. 558.00 g of (2-(chloromethoxy)ethyl)trimethylsilane was added dropwise with a constant pressure dropping funnel at internal temperature of 5° C.-8° C. After the addition of the (2-(chloromethoxy)ethyl)trimethylsilane, the external temperature was set to 20° C., and the reaction solution was stirred for 3 hours. Then 3.2 L of dimethyltetrahydrofuran, 1.8 L of water, 880.00 g of compound 1e, 640.00 g of potassium carbonate and 85.00 g of 1,1-bis(diphenylphosphino)ferrocene-dichloropalladium were further added to the reactor. The external temperature was set to 85° C. after nitrogen was injected into the reactor for displacement for 20 minutes. The reaction solution was stirred for 16 hours at an internal temperature of 80° C.-82° C. After the reaction solution was cooled to an internal temperature of 20° C., 2 L of water and 15 L of n-heptane were added into the reactor while being stirred. After being stirred for 20 minutes, the reaction solution was filtered to obtain a filter cake which was dried to obtain 1200 g of crude compound 1f. Then the crude compound 1f was added into a reactor with a volume of 50 L and 12 L of dimethyltetrahydrofuran was added. Heating was started and the external temperature was set to 80° C. After the solid was dissolved, 360.00 g of activated carbon was added. The reaction solution was stirred for 16 hour at an internal temperature of 80° C. The reaction solution was filtered to obtain a filtrate which was cooled to 15° C.-20° C., and 20 L of n-heptane was added. The reaction solution was stirred at 15° C.-20° C. for 16 hours and filtered to obtain a filter cake which was vacuum-dried to obtain compound 1f.

Step 6

7 L of 1 M tetrabutylammonium fluoride solution in tetrahydrofuran was added to a reactor with a volume of 50 L, and stirring was started at a rotation speed of 150 rpm. 700.00 g of the compound 1f and 77.69 g of ethylenediamine were added sequentially. An external temperature was set to 72° C., and the reaction solution was stirred for 16 hours at an internal temperature of 67° C. 5.6 L of tetrahydrofuran was further added into the reactor, and the reaction solution was stirred at an internal temperature of 40° C. for 2 hours, and then the reaction solution was stirred at 30° C. for 2 hours, and then stirred at 20° C. for 16 hours. The reaction solution was filtered to obtain a filter cake which was added back into the reactor, and 10 L of water and 5 L of ethanol were added and the mixture was stirred at an internal temperature of 60° C. for 16 hours. The reaction solution was filtered immediately to obtain a filter cake which was vacuum-dried to a constant weight to obtain the crystal form A of the compound of formula (I).

$^1$H NMR (400 MHz, DMSO-$d_6$) δ: 8.81 (s, 1H), 8.43 (s, 1H), 8.23 (s, 2H), 7.92 (d, J=8.8 Hz, 2H), 7.80 (s, 1H), 7.77-7.72 (m, 1H), 7.71-7.63 (m, 1H), 7.07 (d, J=8.8 Hz, 2H), 3.79-3.76 (m, 4H), 3.16 (br. s., 4H); MS (ESI) m/z: 412 $[M+H]^+$.

Example 2 Preparation of Crystal Form B of Compound of Formula (I)

(I)

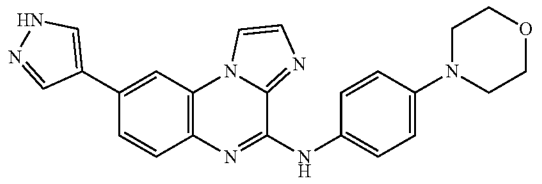

19.1 mg of the solid crystal form A of the compound of formula (I) was weighed and added into a 3.0 mL glass vial, and 0.5 mL of dimethylacetamide was added to dissolve the solid to obtain a clear solution. A 3.0 mL opened glass vial containing the clear solution was placed in a 20 mL glass bottle filled with 3 mL of acetone in advance. After being sealed, the glass bottle was placed at room temperature for three days for gas and liquid penetration, a supernatant was removed with a straw, and a remaining solid was dried at room temperature in the glass bottle which was opened for five days to obtain the solid. Then an appropriate amount of solid was weighed and added into an aluminum crucible with a cover, and the solid was heated from room temperature to 150° C. at a heating rate of 10° C./min under protection of dry nitrogen injected at 50 mL/min, and then cooled down to room temperature. The crystal form B of the compound of formula (I) was obtained via XRPD detection.

Example 3 Preparation of Crystal Form C of Compound of Formula (II-1)

(II-1)

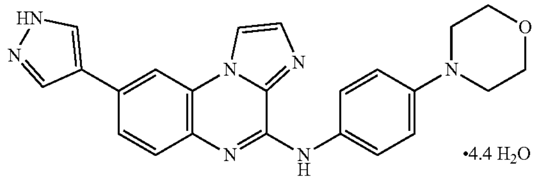

20.1 mg of the solid crystal form A of the compound of formula (I) was weighed and added into a glass vial, 3.0 mL of tetrahydrofuran/water (volume ratio: 4:1) was added to dissolve the solid, and a sample solution was filtered with a polytetrafluoroethylene filter membrane with a 0.45 micron pore size into a new 3.0 mL glass vial to obtain a clear solution which was slowly evaporated at room temperature for three days to obtain a solid when the solvent was removed by evaporation. The crystal form C of the compound of formula (II-1) was obtained via XRPD detection.

Example 4 Preparation of Crystal Form D of Compound of Formula (III-1)

(III-1)

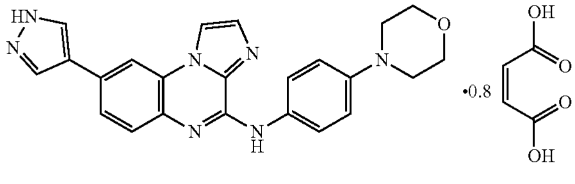

20.4 mg of the solid crystal form A of the compound of formula (I) was weighed and added into a glass vial, 0.5 mL of ethanol/dimethyl sulfoxide (volume ratio: 19:1) was added, and the reaction solution was subjected to magnetic stirring at room temperature (at about 600 rpm), 5.7 mg of maleic acid was added, to obtain a milky white suspension. The milky white suspension was subjected to magnetic stirring at 50° C. (at about 700 rpm) for four days, and after centrifugation, a resulting solid was subjected to vacuum drying at room temperature for two hours to obtain a solid. The crystal form D of the compound of formula (III-1) was obtained via XRPD detection.

Example 5 Preparation of Crystal Form E of Compound of Formula (IV-1)

(IV-1)

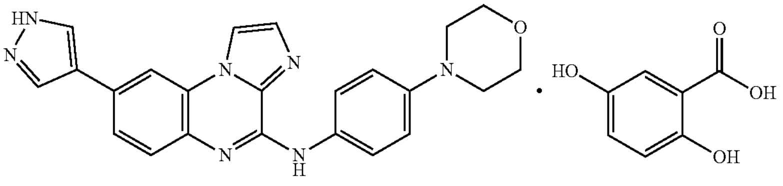

18.4 mg of the solid crystal form A of the compound of formula (I) was weighed and added into a glass vial, 0.5 mL of ethanol/dimethyl sulfoxide (volume ratio: 19:1) was added, and the reaction solution was subjected to magnetic stirring at room temperature (at about 600 rpm), 7.5 mg of gentisic acid was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form E of the compound of formula (IV-1) was obtained via XRPD detection.

Example 6 Preparation of Crystal Form F of Compound of Formula (V-1)

(V-1)

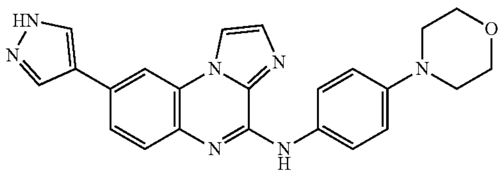

•0.8 HCl 20.8 mg of the solid crystal form A of the compound of formula (I) was weighed and added into a glass vial, 0.5 mL of ethanol/dimethyl sulfoxide (volume ratio: 19:1) was added, and the reaction solution was subjected to magnetic stirring at room temperature (at about 600 rpm), 4.9 μL of concentrated hydrochloric acid was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form F of the compound of formula (V-1) was obtained via XRPD detection.

Example 7 Preparation of Crystal Form G of Compound of Formula (V-2)

(V-2)

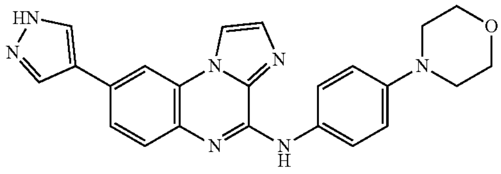

•1.7 HCl 19.3 mg of the solid crystal form A of the compound of formula (I) was weighed and added into an HPLC glass vial, 0.5 mL of tetrahydrofuran/water (volume ratio: 19:1) was added, and the reaction solution was subjected to magnetic stirring at room temperature (at about 600 rpm), 4.9 μL of hydrochloric acid was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form G of the compound of formula (V-2) was obtained via XRPD detection.

Example 8 Preparation of Crystal Form H of Compound of Formula (VI-1)

(VI-1)

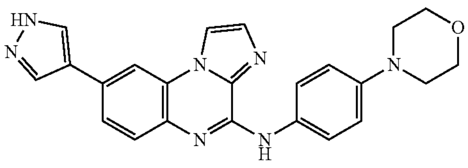

•1.1 $H_2SO_4$ 19.2 mg of the solid crystal form A of the compound of formula (I) was weighed and added into an HPLC glass vial, 0.5 mL of ethanol/dimethyl sulfoxide (volume ratio: 19:1) was added, and a reaction solution was subjected to magnetic stirring at room temperature (at about 600 rpm), 12.2 μL of sulfuric acid was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form H of the compound of formula (VI-1) was obtained via XRPD detection.

Example 9 Preparation of Crystal Form I of Compound of Formula (VII-1)

(VII-1)

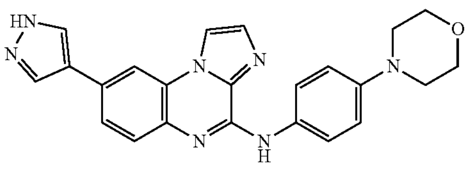

•1.3 $H_3PO_4$ 22.5 mg of the solid crystal form A of the compound of formula (I) was weighed and added into an HPLC glass vial, 0.5 mL of ethanol/dimethyl sulfoxide (volume ratio: 19:1) was added, and the reaction solution was subjected to magnetic stirring at room temperature (at about 600 rpm), 2.6 μL of phosphoric acid was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form I of the compound of formula (VII-1) was obtained via XRPD detection.

Example 10 Preparation of Crystal Form J of Compound of Formula (VII-2)

(VII-2)

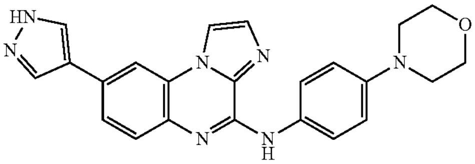

•1.9 $H_3PO_4$ 18.5 mg of the solid crystal form A of the compound of formula (I) was weighed and added into an HPLC glass vial, 0.5 mL of tetrahydrofuran/water (volume ratio: 19:1) was added, and the reaction solution was subjected to magnetic stirring at room temperature (at about 600 rpm), 2.6 μL of phosphoric acid was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form J of the compound of formula (VII-2) was obtained via XRPD detection.

Example 11 Preparation of Crystal Form K of Compound of Formula (VIII-1)

(VIII-1)

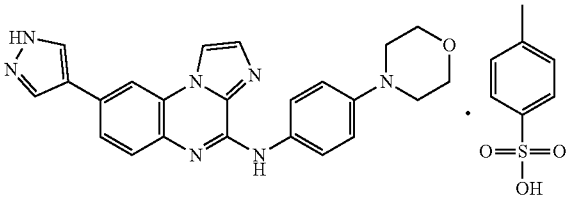

21.3 mg of the solid crystal form A of the compound of formula (I) was weighed and added into an HPLC glass vial, 0.5 mL of ethanol/dimethyl sulfoxide (volume ratio: 19:1) was added, and the reaction solution was subjected to magnetic stirring at room temperature (at about 600 rpm), 8.5 mg of p-toluenesulfonic acid was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form K of the compound of formula (VIII-1) was obtained via XRPD detection.

Example 12 Preparation of Crystal Form L of Compound of Formula (VIII-1)

(VIII-1)

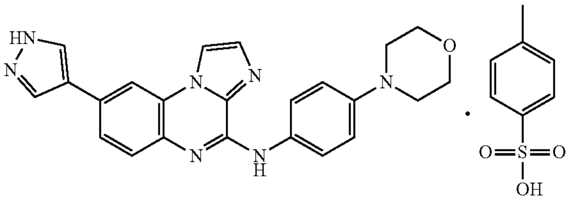

18.6 mg of the solid crystal form A of the compound of formula (I) was weighed and added into an HPLC glass vial, 0.5 mL of tetrahydrofuran/water (volume ratio: 19:1) was added, and the reaction solution was subjected to magnetic stirring at room temperature (at about 600 rpm), 8.3 mg of p-toluenesulfonic acid was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form L of the compound of formula (VIII-1) was obtained via XRPD detection.

Example 13 Preparation of Crystal Form M of Compound of Formula (IX-1)

(IX-1)

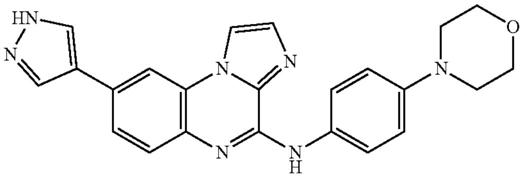

•HBr 18.6 mg of the solid crystal form A of the compound of formula (I) was weighed and added into an HPLC glass vial, 0.5 mL of ethanol/dimethyl sulfoxide (volume ratio: 19:1) was added, and the reaction solution was subjected to magnetic stirring at room temperature (at about 600 rpm), 9.9 mg of 40% hydrobromic acid aqueous solution was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain the solid. The crystal form M of the compound of formula (IX-1) was obtained via XRPD detection.

Example 14 Preparation of Crystal Form N of Compound of Formula (IX-2)

(IX-2)

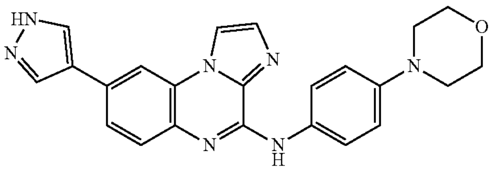

•1.7 HBr 18.9 mg of the solid crystal form A of the compound of formula (I) was weighed and added into an HPLC glass vial, 0.5 mL of tetrahydrofuran/water (volume ratio: 19:1) was added, and the reaction solution was subjected to magnetic stirring at room temperature (at about 600 rpm), 9.8 mg of 40% hydrobromic acid aqueous solution was added, to obtain a yellow suspension. The yellow suspension was subjected to magnetic stirring at 50° C. (at about 700 rpm) for four days, and after centrifugation, a resulting solid was subjected to vacuum drying at room temperature for two hours to obtain a solid. The crystal form N of the compound of formula (IX-2) was obtained via XRPD detection.

CHARACTERIZATION EXAMPLES

Example 1: Solid Stability Test of Crystal Form A of Compound of Formula (I)

According to "Guidelines for the Stability Testing of Drug Substances and Preparations" (General Chapter 9001 in the Chinese Pharmacopoeia, Volume IV, 2015 Edition), in order to evaluate solid stability of the crystal form A of the compound of formula (I), the crystal form A was subjected to stability evaluation with respect to influencing factors (high temperature, high humidity and sunlight) and 60° C./75% RH and 40° C./75% RH conditions. The crystal form A was placed under conditions of high temperature (60° C., sealed) and high humidity (92.5% RH, wrapped in parafilm with 5 pierced small holes) for 1 week and 2 weeks, respectively. According to ICH conditions (total illuminance of visible light reached 1200000 lux·hrs, and total ultraviolet light illuminance reached 200 W·hrs/$m^2$), the crystal form A was sealed and placed under visible light and ultraviolet light (a control group sample was placed in the dark at the same time and wrapped in tinfoil) under 60° C./75% RH (wrapped in parafilm pierced with 5 small holes) for 1 and 2 months, and placed under the condition of 40° C./75% RH (wrapped with parafilm with 5 pierced small holes) for 1, 2 and 3 months. All the stability samples were subjected to XRPD detection to detect changes in crystal forms. The results are shown in Table 19.

About 10 mg of the crystal form was accurately weighed, put in a dry and clean glass bottle, spread into a thin layer, covered with aluminum foil with small pierced holes, and put under conditions of the influencing factor test and accelerated conditions. A sample under sunlight conditions (1200000 Lux visible light, and 200 W ultraviolet light) was put in a transparent glass bottle and fully exposed, and a sample used for XRPD detection was put separately.

After the sample was taken out by a time point, the glass bottle was covered with a lid, sealed with parafilm, and stored in a refrigerator at −20° C. During sample preparation, the sample was taken out of the refrigerator and recovered to room temperature, 10 mL of 80% ACN was added, and the sample was dissolved by ultrasonication for 2 minutes to obtain a solution at a concentration of about 1 mg/mL. A liquid phase was used for sample analysis, and the test result was compared with an initial test result on Day 0. The test results are shown in Table 19 below.

Preparation of a standard solution on Day 0: About 10 mg of the crystal form was weighed, put into a 10 mL volumetric flask, dissolved in 80% acetonitrile and diluted to the scale.

In addition, all the stability samples were subjected to the HPLC tests. Specific results are summarized in Table 19.

TABLE 19

Results of Solid Stability Test of a Crystal Form A of a Compound of Formula (I)

| Test condition | Sampling condition | Purity (area %) | Crystal form |
|---|---|---|---|
| — | Day 0 | 99.05 | Crystal form A |
| High temperature | 1 week | 98.99 | Crystal form A |
| (60° C., opened) | 2 week | 99.10 | Crystal form A |
| High humidity | 1 week | 99.03 | Crystal form A |
| (relative humidity 92.5%, opened) | 2 week | 99.11 | Crystal form A |
| Visible light + ultraviolet light (ICH condition) | Total illuminance of visible light reached 1200000 lux · hrs Total ultraviolet light illuminance reached 300 W · hrs/$m^2$ | 99.12 | Crystal form A |
| Control group kept in the dark | Under both visible light and ultraviolet light, and wrapped with tin foil | 99.12 | Crystal form A |
| High temperature | 1 month | 99.15 | Crystal form A |
| and high humidity | 2 months | 99.03 | Crystal form A |
| (60° C., relative humidity 75%, opened) | | | |
| High temperature | 1 months | 99.12 | Crystal form A |
| and high humidity | 2 months | 99.06 | Crystal form A |
| (40° C., relative | 3 months | 99.04 | Crystal form A |
| humidity 75%, opened) | | | |

Conclusion: The crystal form A of the compound of formula (I) experienced no significant change in purity and crystal form under all stability conditions (high temperature, high humidity and sunlight), and had good chemical stability.

Activity Test

1. In Vitro Evaluation of Inhibitory Activity Against Syk Protein Kinase

Test purpose: to measure an inhibitory $IC_{50}$ value of the compounds against Syk protein kinase.

Test material: Syk kinase (Invitrogen, PV3857)

DTT (Sigma#43815): dithiothreitol

ATP (Sigma#A7699): triphosadenine $MgCl_2$ (Sigma#63020): magnesium chloride $MnCl_2$ (Sigma#M1787): manganese chloride EDTA (Invitrogen#15575-020): ethylenediaminetetraacetic acid HEPES Buffer (Invitrogen#15630-080): zwitterionic sulfonic acid buffer HTRF® KinEASE™ TK (Cisbio#62TK0PEC, 20000 tests): HTRF kinase kit Low volume, 384-well, white polystyrene plate (Greiner#784075)

384-well microplates (Greiner#781946)

Centrifuge (Eppendorf#5810R)

Micropipette (Eppendorf)

Pipette (Greiner)

Pipettor (Eppendorf)

Mutidorp injector

POD 810 Plate Assembler Fully Automatic Microplate Pretreatment System

Envision Reader

Test Procedure and Method:

(a) Compound dilution and microplate injection
  1) Compound powder was weighed and dissolved in a specific amount of DMSO at an initial concentration of 10 mM.
  2) The compound was diluted to have a concentration of 0.74 mM, POD18 was used for microplate injection by 135 nL per well, an initial concentration of the compound was 10 μM, and 11 concentrations and 3-fold descending serial dilution were carried out.

(b) Reaction stage of enzyme and substrate
  1) Preparation of test buffer dilution: 5×HTRF buffer in the kit was diluted to 1×HTRF buffer, and a specified amount of DTT and $MgCl_2$ solution were added for later use.
  2) A Syk enzyme reaction solution was prepared with 1×HTRF buffer, so that a final reaction concentration of Syk kinase was 0.0156 ng/μL.
  3) A TK-Substrate-biotin/ATP mixture was prepared, so that a final substrate concentration was controlled to be 0.2 μM. An ATP concentration was controlled to be 2 μM.
  4) A mutidorp injector was used to add the sample, 5 μL of Syk enzyme solution and TK-Substrate-biotin/ATP mixture were added to each well, and incubated at 23° C. for 1 hour.

(c) Test phase:
  1) 13.33 mL of ethylenediaminetetraacetic acid solution was added to the test buffer of the kit, and specified amounts of Eu-labeled antibody and XL-665 were added, to prepare the test solution.
  2) The sample was added with a mutidorp injector, and 10 μL of the test solution was added to each well and incubated at 23° C. for 1 hour. A reaction of the mixture of enzyme and substrate was quenched.
  3) Values on the Envision Reader were read after centrifugation.

(d) Data analysis: XL-Fit was used to analyze data, and the $IC_{50}$ value of the compound was calculated. The results are shown in Table 20.

Test results:

TABLE 20

Test Results of Inhibitory Activity Against Syk

| Compound | $IC_{50}$ (nM) against Syk |
|---|---|
| Crystal form A of a compound of formula (I) | 25 |

Conclusion: The crystal form A of the compound of formula (I) had good inhibitory activity against Syk.

2. In Vitro Evaluation of Inhibitory Activity Against KDR (VEGFR-2) Protein Kinase Teat Purpose The KDR Kinase Kit was designed to use Kinase-Glo® MAX as a teat reagent to measure KDR kinase activity, and the $IC_{50}$ value of the compound was used as an indicator for compound screening and analysis.

Test Method and Procedure

ADP-GLO™ Kinase Assay is an assay reaction for measuring adenosine diphosphate formed by the kinase by using a luminescent kinase; and ADP was converted into ATP, that is, conversion into a light signal via Ultra-Glo™ Luciferase. The light signal was positively correlated with the quantity of ADP and kinase activity. Such assay was very suitable for determining the activity of the compound, making the assay ideal for primary screening and a kinase selectivity assay. The ADP-Glo™ Kinase Assay can be used to monitor the activity of almost all ADP-producing enzymes (for example, a kinase or ATPase):

1) Enzyme, substrate, ATP and inhibitors were diluted in kinase buffer;
2) 384-well plate: 1 μL of inhibitor or (5% dimethyl sulfoxide solution) 2 μL of KDR enzyme, and 2 μL of substrate/ATP mixture;
3) The 384-well plate was incubated at room temperature for 60 minutes;
4) 5 μL of ADP-GLO™ reagent was added;
5) The 384-well plate was incubated at room temperature for 40 minutes;
6) 10 μL of kinase test reagent was added;
7) The 384-well plate was incubated at room temperature for 30 minutes;
8) Lumination (integration time: 0.5 to 1 second) was recorded. Data was represented by a relative light unit (rlu), was directly correlated with an amount of ATP produced, and indicated correlation between a percentage of ATP converted into ADP for each kinase and a corresponding signal-to-background ratio.
9) Data analysis: (a) The KDR enzyme was titrated with 50 μM of ATP to display a light signal indicating production of the KDR enzyme; and (b) 1.5 ng of KDR was used to generate staurosporine dose-response to determine the $IC_{50}$ value of the inhibitor. The results are shown in Table 21 below.

Test Result

TABLE 21

Test Results of Inhibitory Activity Against KDR

| Compound | $IC_{50}$ (nM) against KDR |
|---|---|
| Crystal form A of a compound of formula (I) | 28 |

Conclusion: The crystal form A of the compound of formula (I) had good inhibitory activity against KDR (VEGFR-2).

3. Pharmacokinetic Evaluation

Test purpose: to study pharmacokinetics of the compound in eye tissues of male SD rats after single administration of eye drop Test material: SD rats (male, 7 to 10 weeks of age, WTLH/SLAC)

Test operation: In this test, 18 male SD rats were provided by Beijing Vital River Laboratory Animal Technology Co., Ltd., and were randomly divided into 6 groups (3 rats/group), and each group of animals were given 0.730 μM (5 mg/mL for both eyes, 30 μL/eye) of OT202 eye drops during single administration. All animals were not fasted before administration. Details about administration and blood sampling of the crystal form A of a compound of formula (I) are shown in Table 22 and Table 23 below, respectively.

TABLE 22

Parameters of Male SD Rats during Single Administration of Eye Drop

| | | Treatment | | | | | | |
|---|---|---|---|---|---|---|---|---|
| Group # | Male/ Quantity | Test preparation | Batch No. | Strength (mg/mL) | Dose volume | Administration position | Route of administration | Administration frequency |
| 01 | 3 | OT202 eye drop | 20090102 | 5 | 30 μL/ eye | Both eyes | Dripped into an eye | Once |
| 02 | 3 | OT202 eye drop | 20090102 | 5 | 30 μL/ eye | Both eyes | Dripped into an eye | Once |
| 03 | 3 | OT202 eye drop | 20090102 | 5 | 30 μL/ eye | Both eyes | Dripped into an eye | Once |
| 04 | 3 | OT202 eye drop | 20090102 | 5 | 30 μL/ eye | Both eyes | Dripped into an eye | Once |
| 05 | 3 | OT202 eye drop | 20090102 | 5 | 30 μL/ eye | Both eyes | Dripped into an eye | Once |
| 06 | 3 | OT202 eye drop | 20090102 | 5 | 30 μL/ eye | Both eyes | Dripped into an eye | Once |

TABLE 23

Blood Sampling Scheme After Single Administration of Eye Drop in Male SD Rats

| Group | Animal number | Matrix | Sampling time point (h) |
|---|---|---|---|
| 01 | R01, R02 and R03 | Plasma, bulbar conjunctiva, aqueous humor of anterior chamber, cornea, and upper and lower eyelids | 0.5 |
| 02 | R04, R05 and R06 | Plasma, bulbar conjunctiva, aqueous humor of anterior chamber, cornea, and upper and lower eyelids | 1 |
| 03 | R07, R08 and R09 | Plasma, bulbar conjunctiva, aqueous humor of anterior chamber, cornea, and upper and lower eyelids | 3 |
| 04 | R10, R11 and R12 | Plasma, bulbar conjunctiva, aqueous humor of anterior chamber, cornea, and upper and lower eyelids | 6 |
| 05 | R13, R14 and R15 | Plasma, bulbar conjunctiva, aqueous humor of anterior chamber, cornea, and upper and lower eyelids | 12 |
| 06 | R16, R17 and R18 | Plasma, bulbar conjunctiva, aqueous humor of anterior chamber, cornea, and upper and lower eyelids | 24 |

Relevant parameters of pharmacokinetics of the crystal form A of the compound of formula (I) in SD rats are shown in Table 24 below.

TABLE 24

Test Results of Pharmacokinetics

| Matrix | Plasma | Aqueous humor of anterior chamber | Bulbar conjunctiva | Cornea | Upper and lower eyelids |
|---|---|---|---|---|---|
| Sampling range (h) for $T_{1/2}$ calculation | 1-6 | 6-24 | 1-24 | 1-24 | 1-24 |

TABLE 24-continued

| Test Results of Pharmacokinetics | | | | | |
|---|---|---|---|---|---|
| Matrix | Plasma | Aqueous humor of anterior chamber | Bulbar conjunctiva | Cornea | Upper and lower eyelids |
| $C_{max}$ (nM) | 1.23 | 560 | 4510 | 1590 | 10400 |
| $T_{max}$ (h) | 1.00 | 0.500 | 0.500 | 0.500 | 0.500 |
| $T_{1/2}$ (h) | 4.80* | 12.3 | 5.12* | 4.84 | 9.45 |
| $T_{last}$ (h) | 6.00 | 24.0 | 24.0 | 24.0 | 24.0 |
| $AUC_{0\text{-}last}$ (nM · h) | 5.32 | 657 | 15500 | 2530 | 65500 |
| $AUC_{0\text{-}inf}$ (nM · h) | 9.56 | 711 | 16400 | 2590 | 80000 |
| $MRT_{0\text{-}last}$ (h) | 2.98 | 3.35 | 5.28 | 5.05 | 8.40 |
| $MRT_{0\text{-}inf}$ (h) | 7.39 | 6.27 | 6.73 | 5.74 | 13.7 |
| $AUC_{0\text{-}inf}/AUC_{0\text{-}last}$ (%) | 180 | 108 | 106 | 102 | 122 |
| AUC ratio | — | 123 | 2910 | 476 | 12300 |

$C_{max}$: maximum concentration; $T_{max}$: time to peak concentration; $T_{1/2}$: elimination half-life; $T_{last}$: time to last measurable concentration; $AUC_{0\text{-}last}$: area under the plasma concentration-time curve from time 0 to the last quantifiable time point; $AUC_{0\text{-}inf}$: area under the plasma concentration-time curve from time 0 to infinity (extrapolated); $MRT_{0\text{-}last}$: mean residence time from time 0 to the last quantifiable time point; $MRT_{0\text{-}inf}$: mean residence time from time 0 to infinity (extrapolated); AUC ratio: tissue $AUC_{0\text{-}last}$/plasma $AUC_{0\text{-}last}$.
*A linear regression coefficient of an elimination phase of a drug concentration was less than 0.9.
—: not applicable.

Conclusion: The crystal form A of the compound of formula (I) had good pharmacokinetic features, including a good eye-to-blood ratio, tissue exposure and so on.

What is claimed is:

1. A crystal form A of a compound of formula (I), wherein an X-ray powder diffraction pattern of the crystal form A under Cu Kα radiation has characteristic diffraction peaks at 2θ angles of 11.96±0.20°, 14.14±0.20°, 16.76±0.20°, 17.55±0.20°, and 21.84±0.20°,

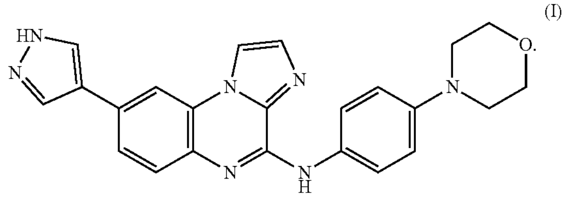 [SMILES: c1cn2c(n1)c(Nc1ccc(N3CCOCC3)cc1)nc1ccc(-c3cn[nH]c3)cc12]
(I)

2. The crystal form A according to claim 1, wherein an X-ray powder diffraction pattern of the crystal form A under Cu Kα radiation has characteristic diffraction peaks at 2θ angles of 11.96±0.20°, 14.14±0.20°, 15.36±0.20°, 16.76±0.20°, 17.55±0.20°, 21.84±0.20°, 23.49±0.20°, and 24.42±0.20°.

3. The crystal form A according to claim 1, wherein an XRPD pattern of the crystal form A is shown in FIG. 1.

4. The crystal form A according to claim 1, wherein a differential scanning calorimetry curve of the crystal form A has an endothermic peak at 332.4° C.±3° C.

Figure 2:
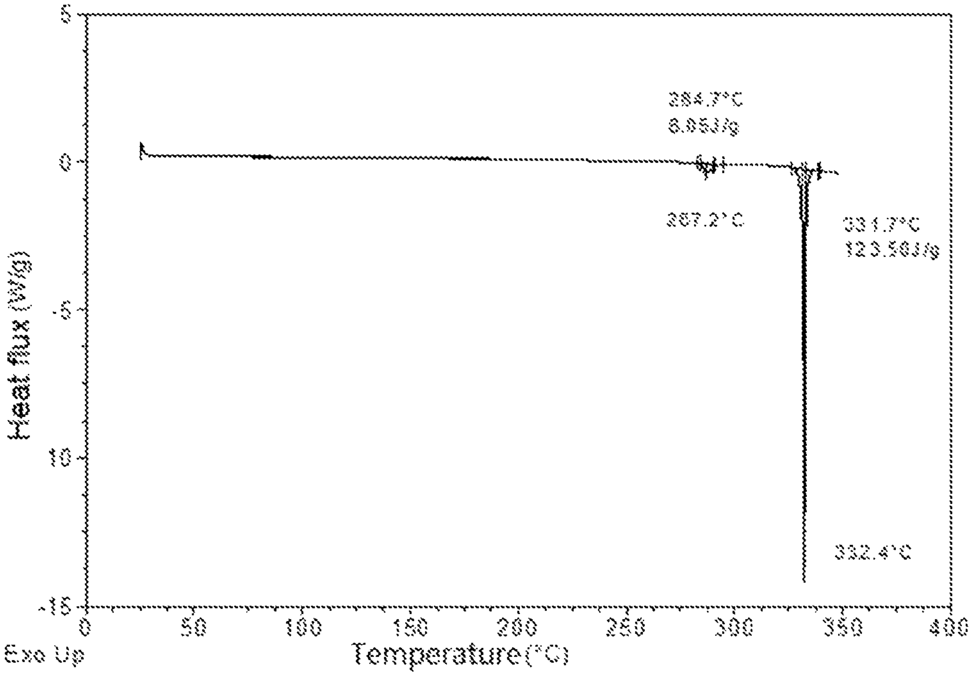
FIG. 2 is a DSC pattern of a crystal form A of a compound of formula (I)

5. The crystal form A according to claim 4, wherein a DSC pattern of the crystal form A is shown in FIG. 2.

6. The crystal form A according to claim 1, wherein a thermal gravimetric analysis curve of the crystal form A has a weight loss of 2.41±0.20% at 250.0° C.±3° C.

Figure 3:
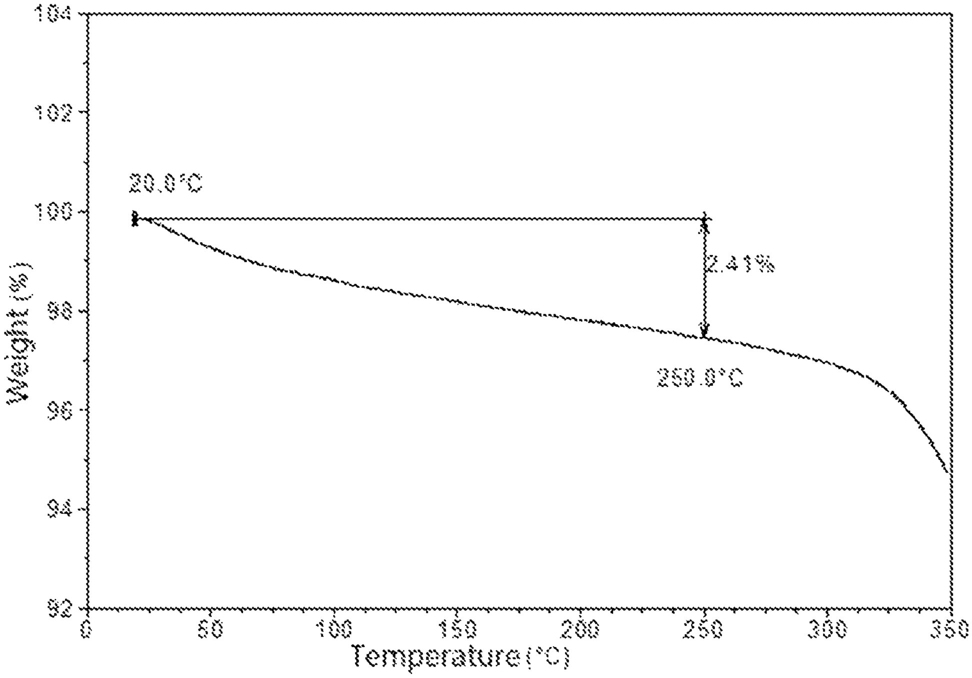
FIG. 3 is a TGA pattern of a crystal form A of a compound of formula (I)

7. The crystal form A according to claim 6, wherein a TGA pattern of the crystal form A is shown in FIG. 3.

8. A crystal form B of a compound of formula (I), wherein an X-ray powder diffraction pattern of the crystal form B under Cu Kα radiation has characteristic diffraction peaks at 2θ angles of 12.14±0.20°, 19.52±0.20°, 22.08±0.20°, and 28.22±0.20°,

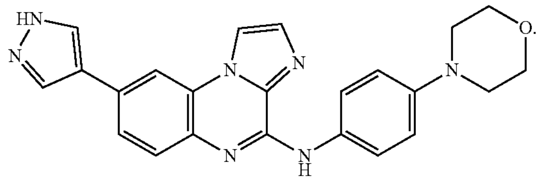
(I)

Figure 4:
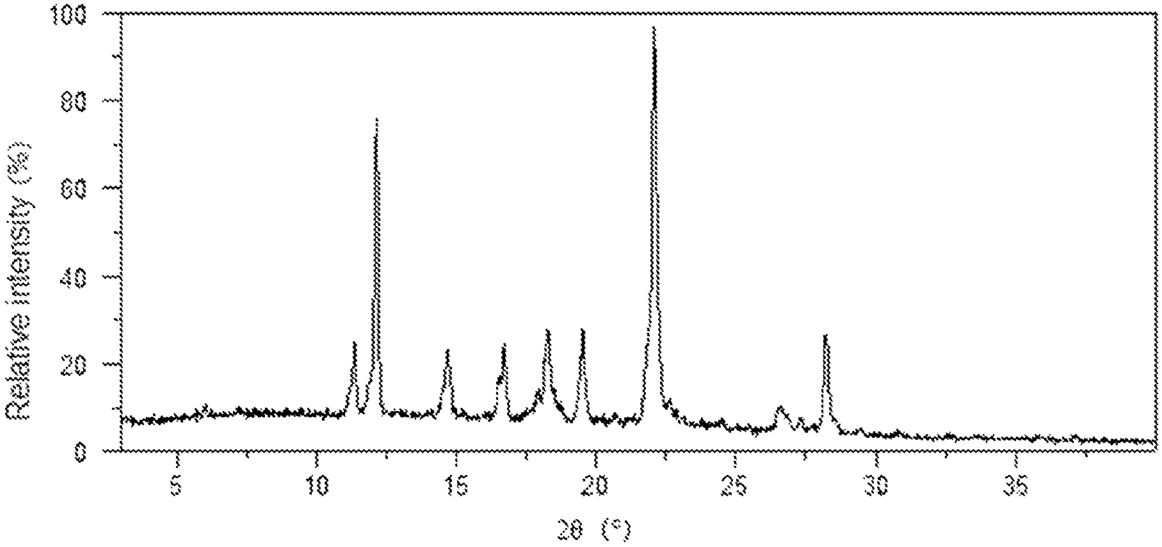
FIG. 4 is an XRPD pattern of a crystal form B of a compound of formula (I)

9. The crystal form B according to claim 8, wherein an XRPD pattern of the crystal form B is shown in FIG. 4.

10. The crystal form B according to claim 9, wherein a differential scanning calorimetry curve of the crystal form B has an endothermic peak at 331.8° C.±3° C.

Figure 5:
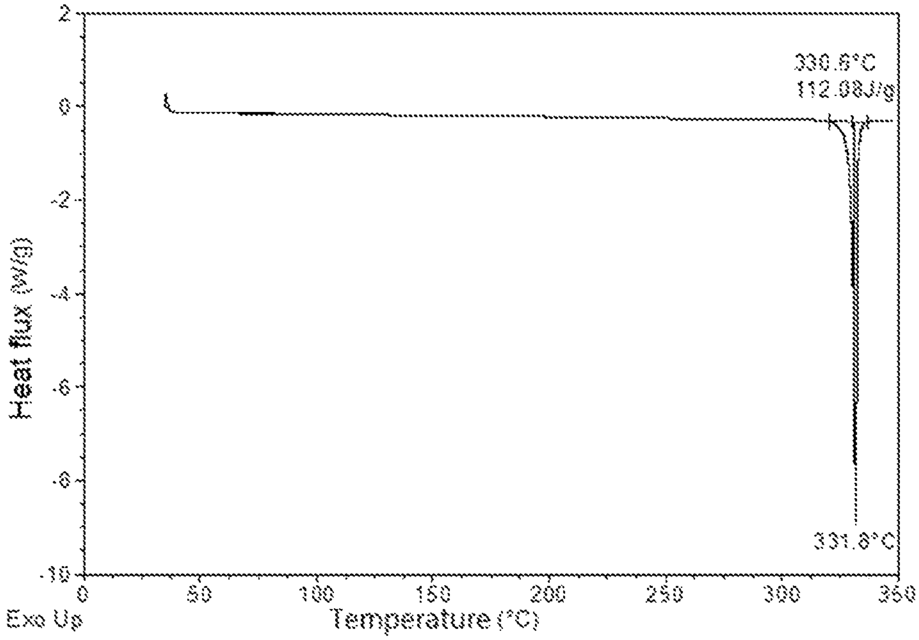
FIG. 5 is a DSC pattern of a crystal form B of a compound of formula (I)

11. The crystal form B according to claim 10, wherein a DSC pattern of the crystal form B is shown in FIG. 5.

12. The crystal form B according to claim 9, wherein a thermal gravimetric analysis curve of the crystal form B has a weight loss of 4.11±0.20% at 300.0° C.±3° C.

Figure 6:
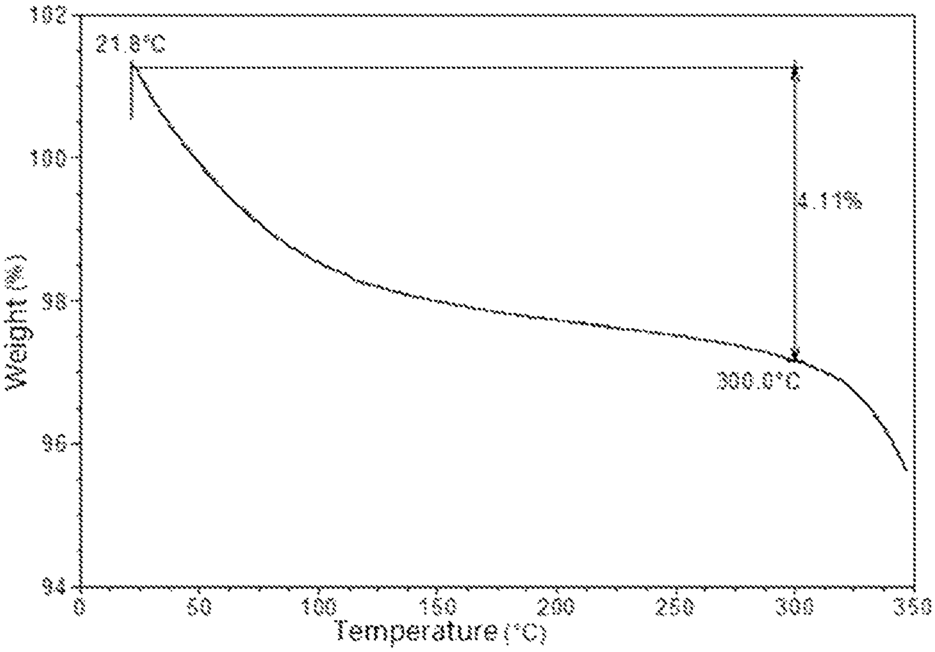
FIG. 6 is a TGA pattern of a crystal form B of a compound of formula (I)

13. The crystal form B according to claim 12, wherein a TGA pattern of the crystal form B is shown in FIG. 6.

14. The crystal form B according to claim 9, wherein a preparation method of the crystal form B comprises:

(a) dissolving a crystal form A of the compound of formula (I) in dimethylacetamide wherein an X-ray powder diffraction pattern of the crystal form A under Cu Kα radiation has characteristic diffraction peaks at 2θ angles of 11.96±0.20°, 14.14±0.20°, 16.76±0.20°, 17.55±0.20°, and 21.84±0.20°;
(b) placing an opened glass vial containing a solution of the compound in a glass bottle filled with acetone in advance;
(c) sealing the glass bottle and allowing gas and liquid permeation at 20° C. to 30° C. for three days;
(d) removing a supernatant with a straw, and drying a remaining solid at room temperature in the bottle which is opened for five days to obtain the solid;
(e) adding the solid into an aluminum crucible with a cover and slowly heating the solid to 150° C. under an atmosphere of dry nitrogen; and
(f) cooling the solid down to 20° C. to 30° C.

Figure 7:
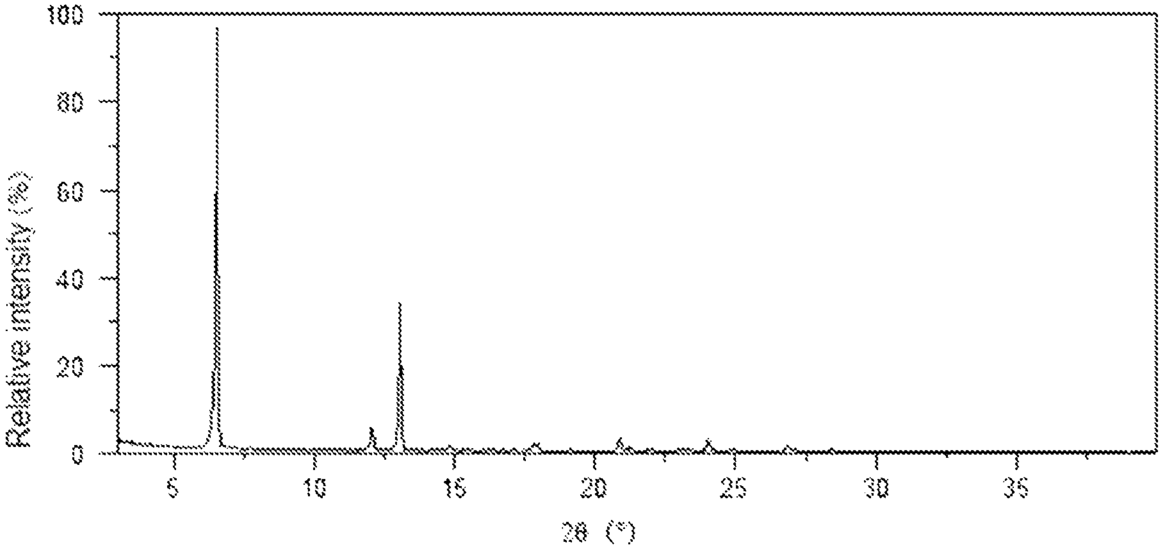
FIG. 7 is an XRPD pattern of a crystal form C of a compound of formula (II-1)
Figure 8:
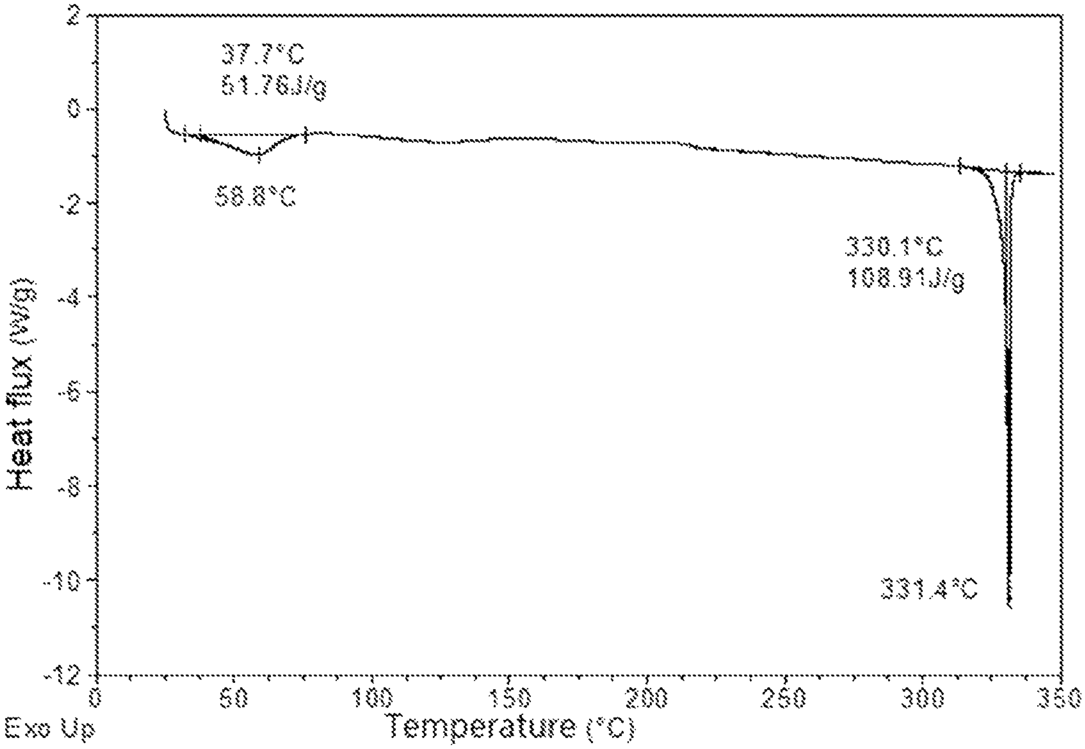
FIG. 8 is a DSC pattern of a crystal form C of a compound of formula (II-1)
Figure 9:
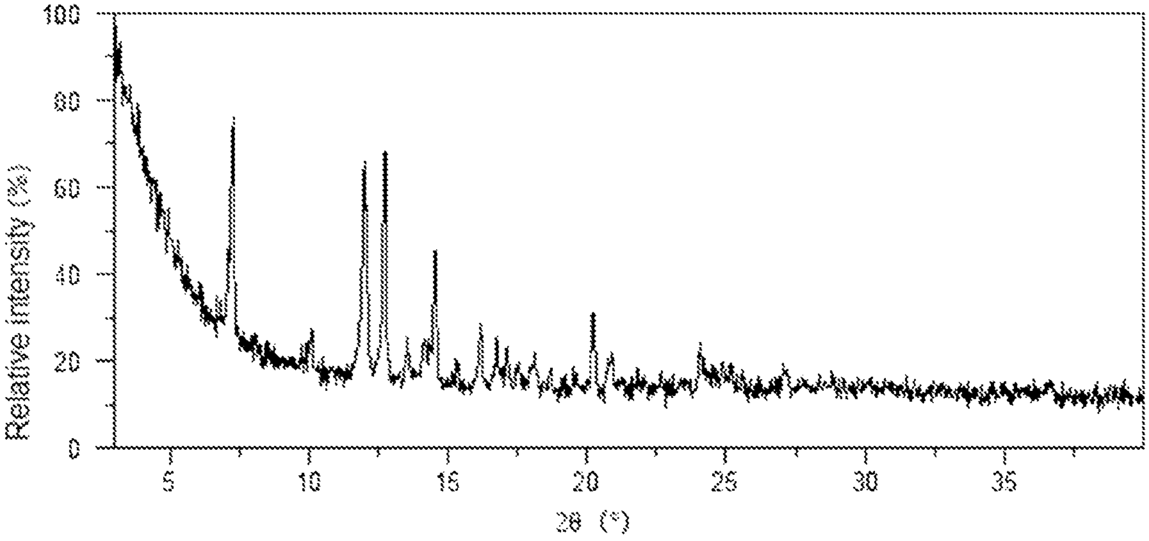
FIG. 9 is an XRPD pattern of a crystal form D of a compound of formula (III-1)
Figure 10:
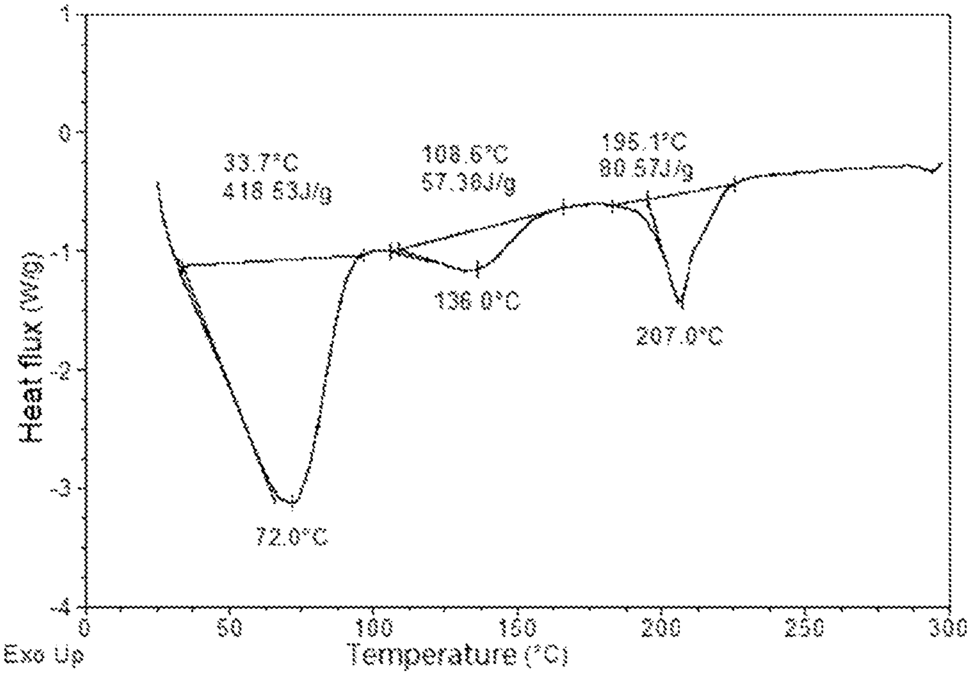
FIG. 10 is a DSC pattern of a crystal form D of a compound of formula (III-1)
Figure 11:
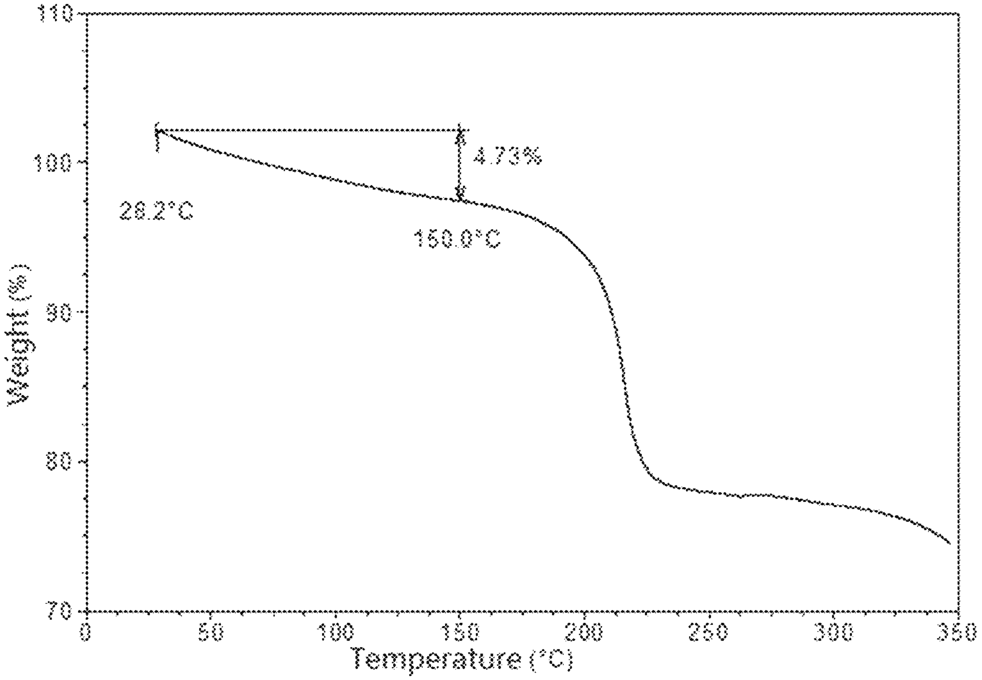
FIG. 11 is a TGA pattern of a crystal form D of a compound of formula (III-1)
Figure 12:
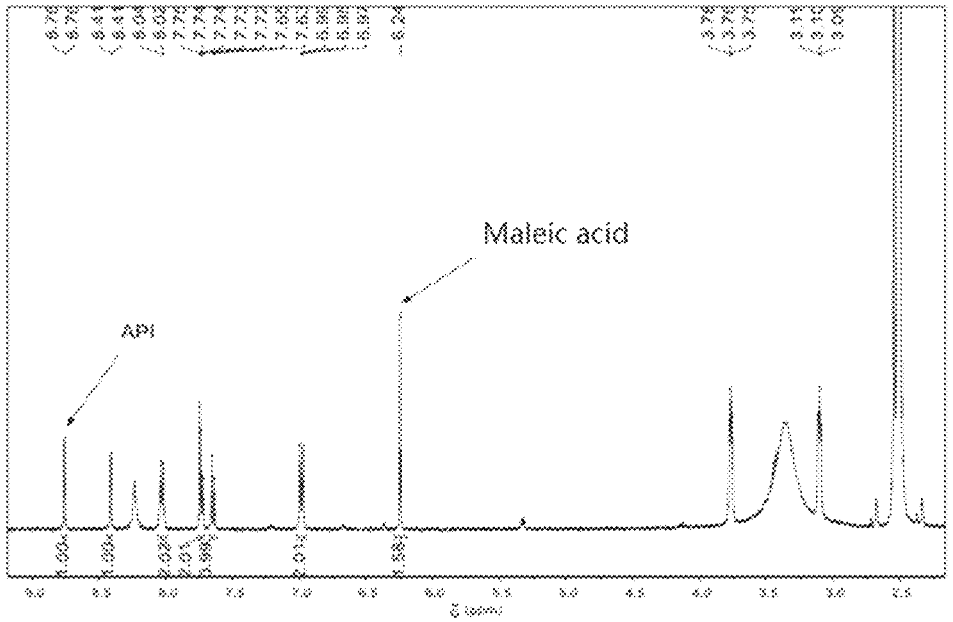
FIG. 12 is an 1H NMR pattern of a crystal form D of a compound of formula (III-1)
Figure 13:
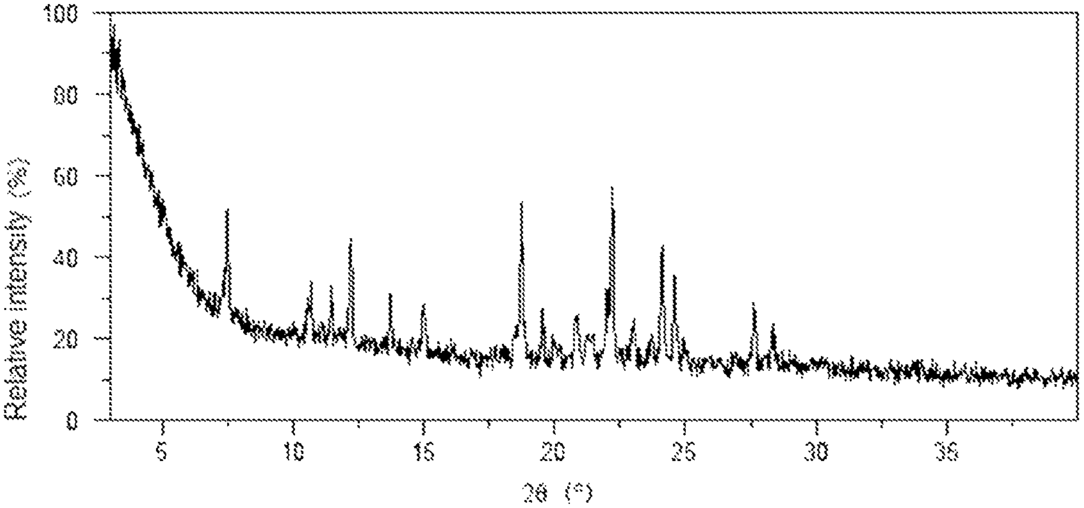
FIG. 13 is an XRPD pattern of a crystal form E of a compound of formula (IV-1)
Figure 14:
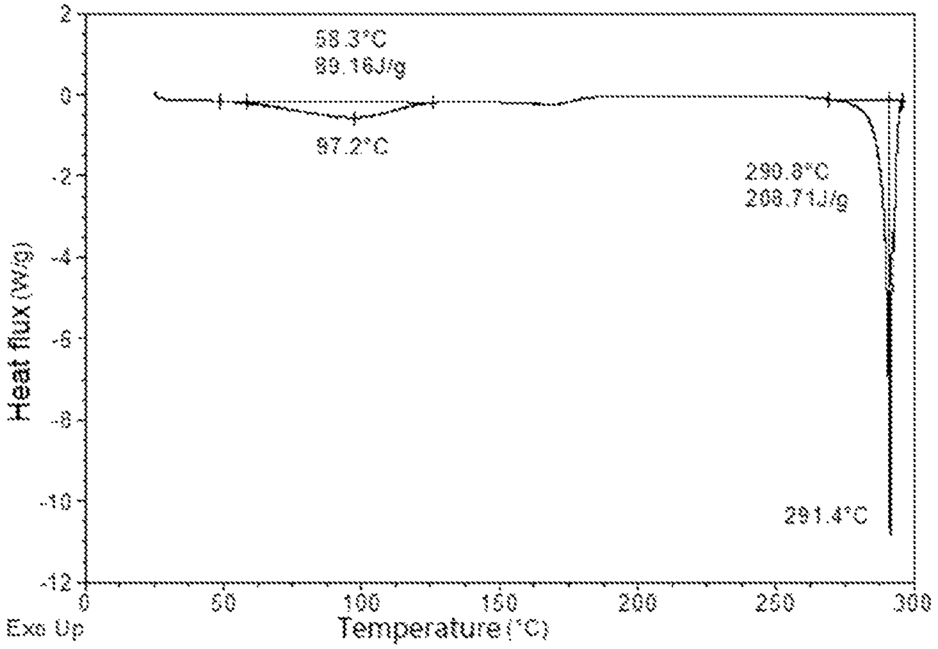
FIG. 14 is a DSC pattern of a crystal form E of a compound of formula (IV-1)
Figure 15:
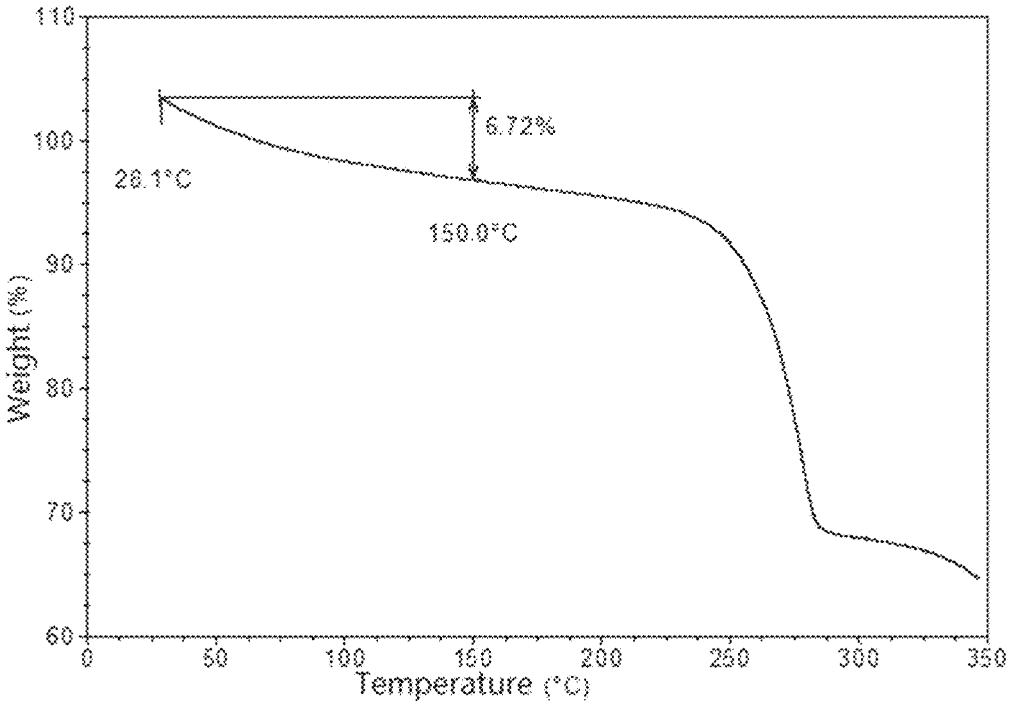
FIG. 15 is a TGA pattern of a crystal form E of a compound of formula (IV-1)
Figure 16:
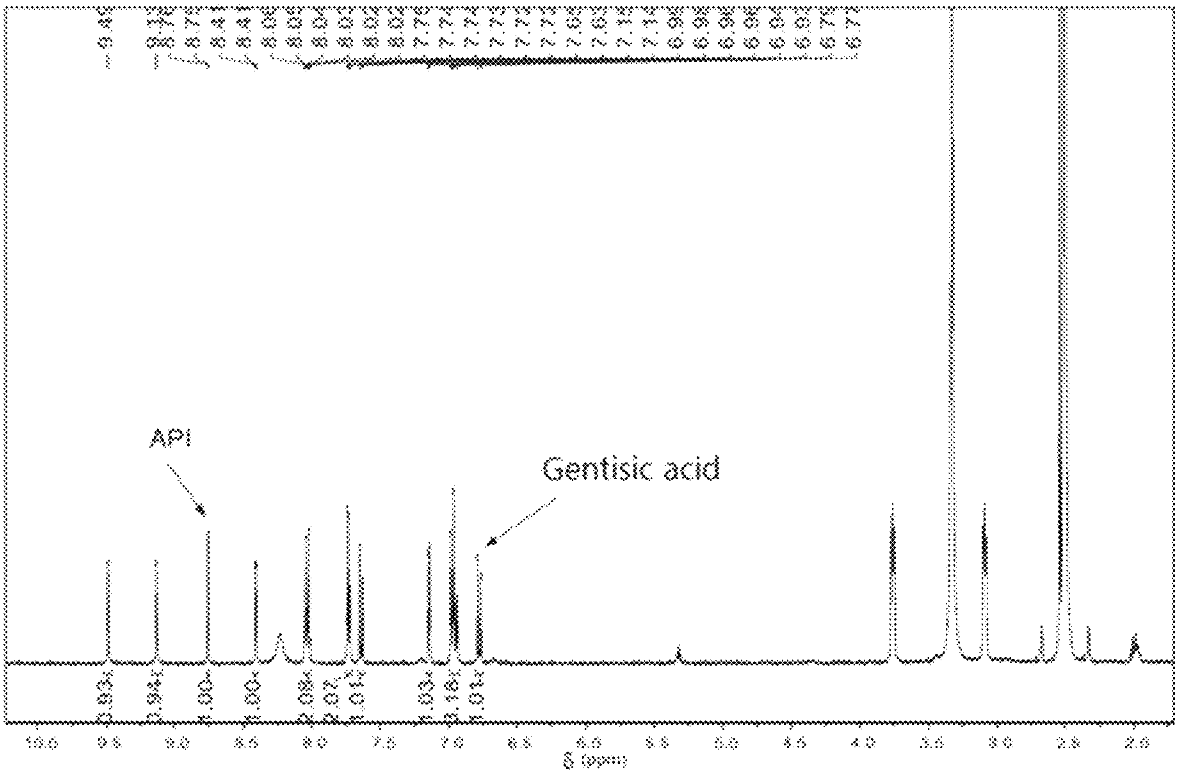
FIG. 16 is an 1H NMR pattern of a crystal form E of a compound of formula (IV-1)
Figure 17:
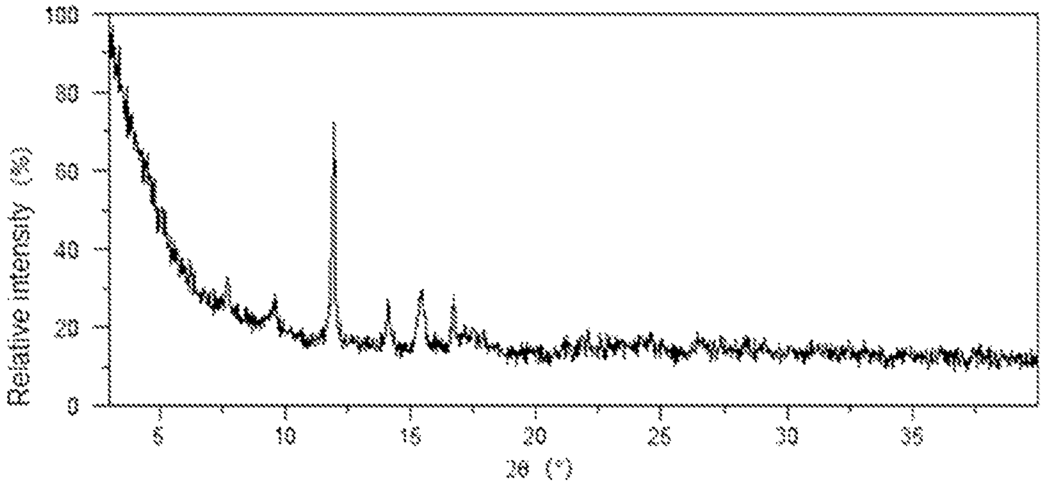
FIG. 17 is an XRPD pattern of a crystal form F of a compound of formula (V-1)
Figure 18:
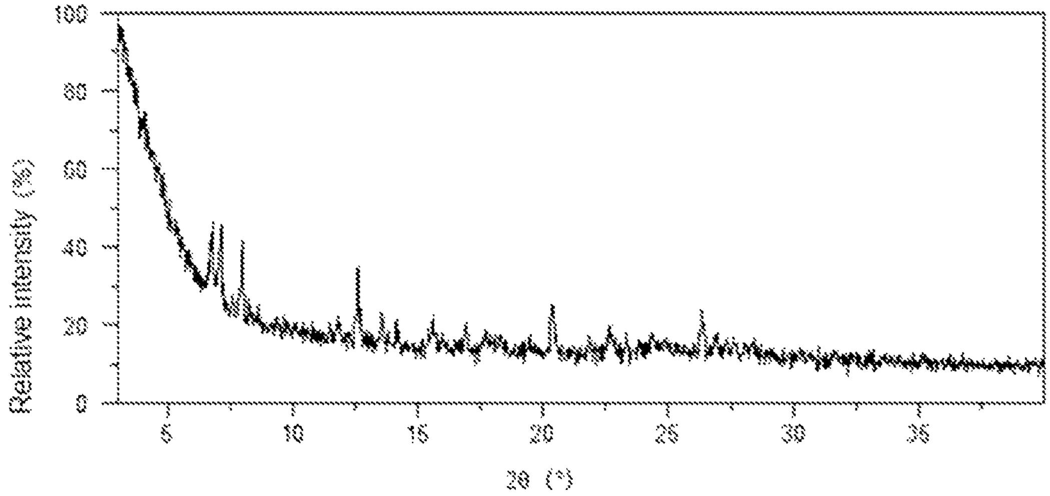
FIG. 18 is an XRPD pattern of a crystal form G of a compound of formula (V-2)
Figure 19:
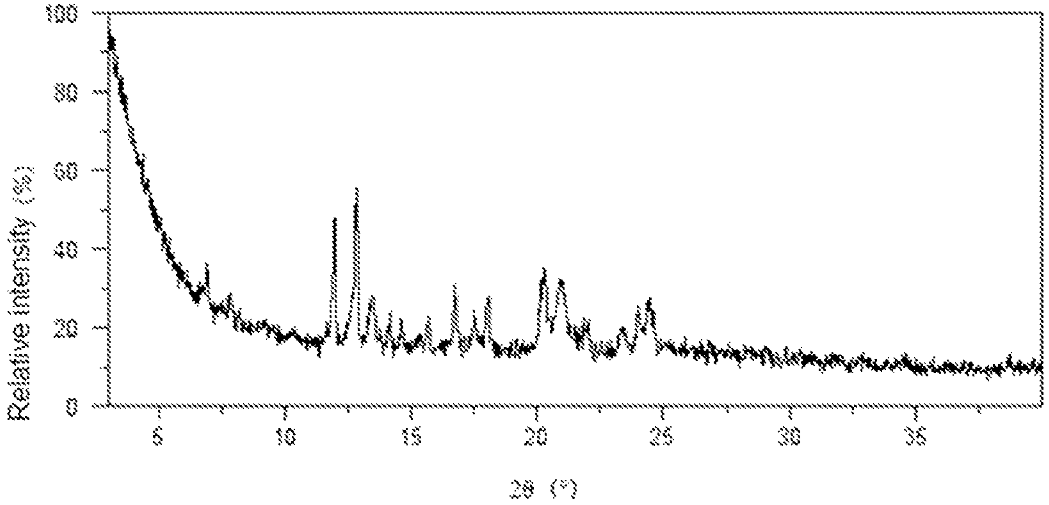
FIG. 19 is an XRPD pattern of a crystal form H of a compound of formula (VI-1)
Figure 20:
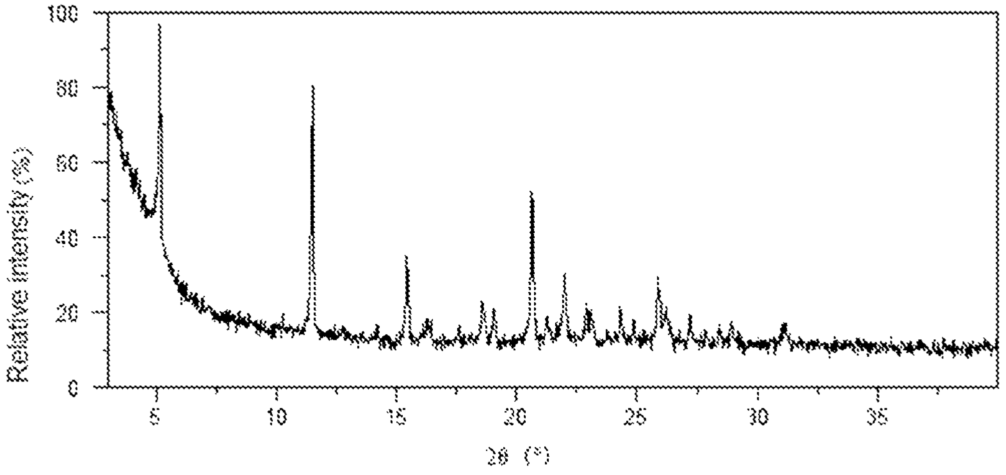
FIG. 20 is an XRPD pattern of a crystal form I of a compound of formula (VII-1)
Figure 21:
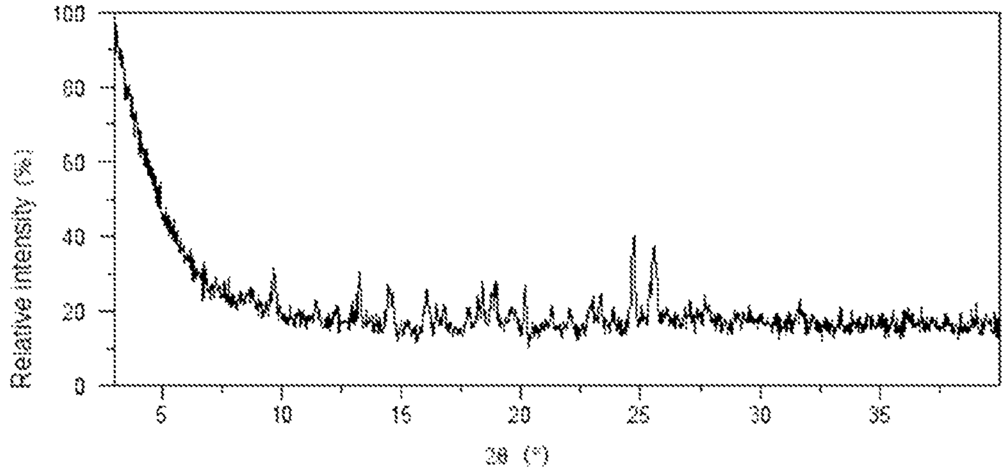
FIG. 21 is an XRPD pattern of a crystal form J of a compound of formula (VII-2)
Figure 22:
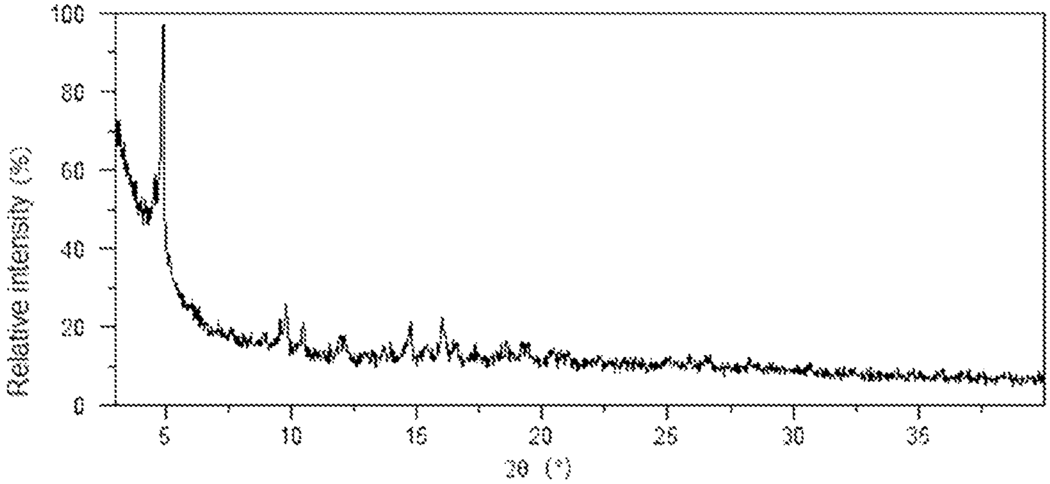
FIG. 22 is an XRPD pattern of a crystal form K of a compound of formula (VIII-1)
Figure 23:
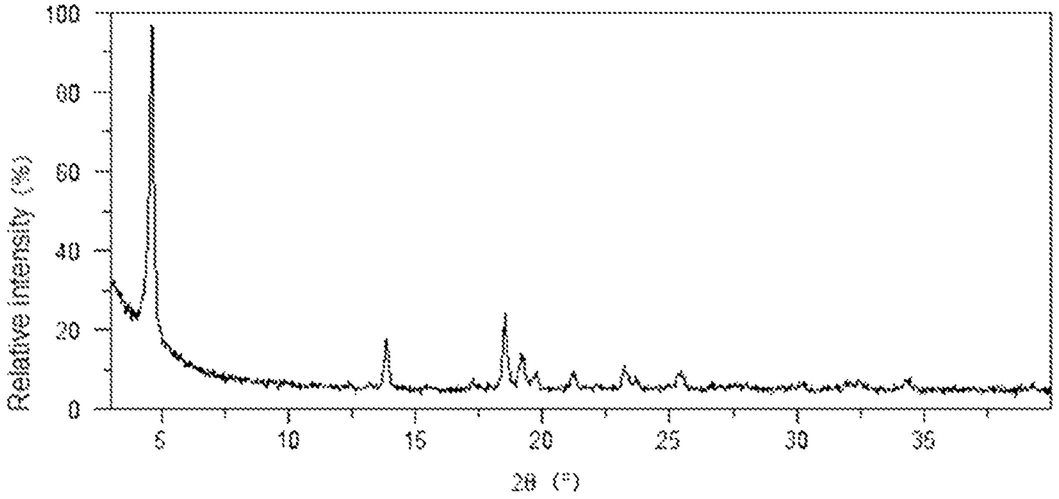
FIG. 23 is an XRPD pattern of a crystal form L of a compound of formula (VIII-1)
Figure 24:
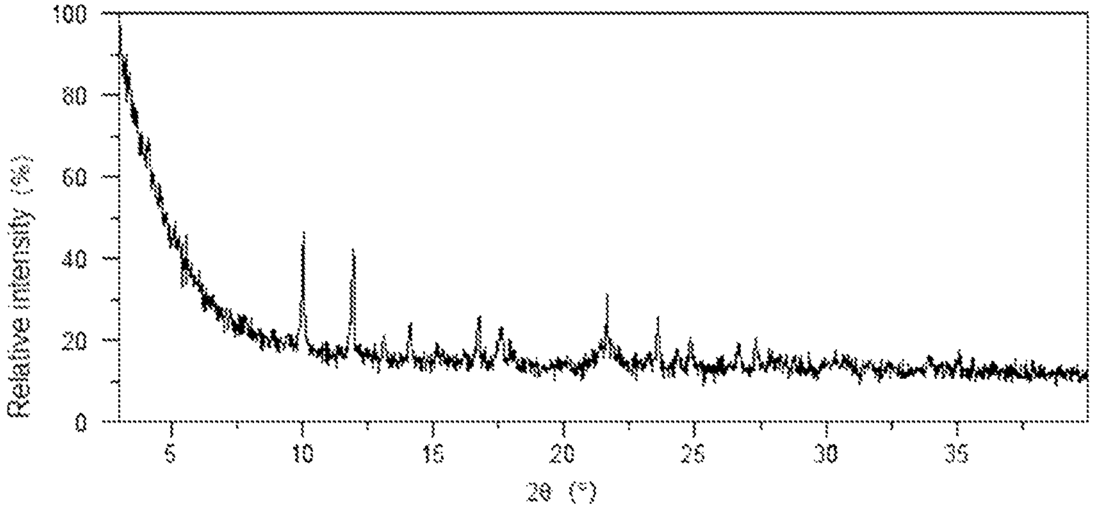
FIG. 24 is an XRPD pattern of a crystal form M of a compound of formula (IX-1)
Figure 25:
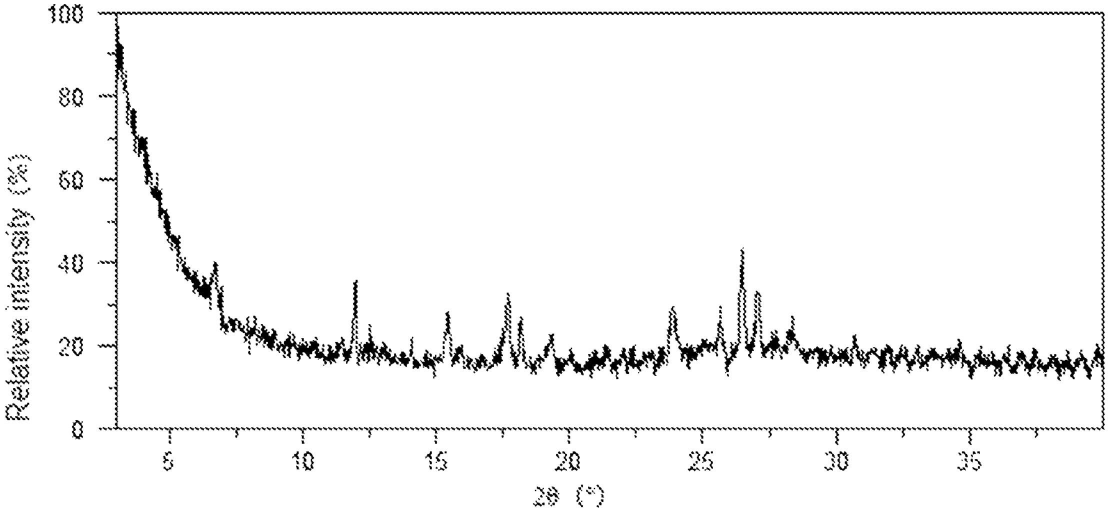
FIG. 25 is an XRPD pattern of a crystal form N of a compound of formula (IX-2).

15. A crystal form C of a compound of formula (II-1), wherein an X-ray powder diffraction pattern of the crystal form C under Cu Kα radiation has characteristic diffraction peaks at 2θ angles of 6.53±0.20°, 12.05±0.20°, and 13.05±0.20°,
(II-1)
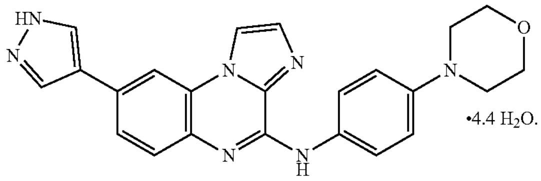
•4.4 $H_2O$.
16. The crystal form C according to claim 15, wherein an XRPD pattern of the crystal form C is shown in FIG. 7.
17. The crystal form C according to claim 15, wherein a DSC pattern of the crystal form C is shown in FIG. 8.
* * * * *